United States Patent
Janson et al.

(10) Patent No.: US 10,058,480 B2
(45) Date of Patent: Aug. 28, 2018

(54) DEVICE CONTAINER

(71) Applicant: Bioverativ Therapeutics Inc., Waltham, MA (US)

(72) Inventors: Christine P. Janson, Dedham, MA (US); Ethan B. Jacoby, Wellesley Hills, MA (US); Frederick Carel Steinmann, Milford, MA (US); Nikhil Gandhi, Holliston, MA (US); Chad Presher, Manchester, NH (US)

(73) Assignee: Bioverativ Therapeutics, Inc., Waltham, MA (US)

( * ) Notice: Subject to any disclaimer, the term of this patent is extended or adjusted under 35 U.S.C. 154(b) by 637 days.

(21) Appl. No.: 14/411,739

(22) PCT Filed: Jul. 3, 2013

(86) PCT No.: PCT/US2013/049322
§ 371 (c)(1),
(2) Date: Dec. 29, 2014

(87) PCT Pub. No.: WO2014/008397
PCT Pub. Date: Jan. 9, 2014

(65) Prior Publication Data
US 2015/0164743 A1    Jun. 18, 2015

Related U.S. Application Data

(60) Provisional application No. 61/667,550, filed on Jul. 3, 2012.

(51) Int. Cl.
*A61J 1/05*        (2006.01)
*B65D 21/02*    (2006.01)
(Continued)

(52) U.S. Cl.
CPC ............... *A61J 1/05* (2013.01); *A61M 5/002* (2013.01); *A61M 5/008* (2013.01);
(Continued)

(58) Field of Classification Search
CPC ......... A61J 1/05; A61J 1/2096; B65D 43/162; B65D 25/10; B65D 43/16; A61M 5/002;
(Continued)

(56) References Cited

U.S. PATENT DOCUMENTS 1,235,890 A      8/1917   Gilbert
1,520,444 A  *  12/1924   Romadka ............... A61F 17/00
                                                                  206/233

(Continued)

FOREIGN PATENT DOCUMENTS

FR      2781145 A1    1/2000
GB    2 372 031 A      8/2002
(Continued)

OTHER PUBLICATIONS

European Search Report for European Patent Application No. EP 13 81 2479, European Patent Office, Munich, Germany, 7 pages, dated Mar. 17, 2016.
(Continued)

*Primary Examiner* — Steven A. Reynolds
(74) *Attorney, Agent, or Firm* — Sterne, Kessler, Goldstein & Fox P.L.L.C.

(57) ABSTRACT

Device containers, such as therapeutic kit containers, are disclosed. In one embodiment, a device container includes a first member configured to releasably hold a syringe barrel, a second member configured to releasably hold a vial, wherein the second member is coupled to the first member by a first hinge, and a third member configured to releasably hold a vial adapter, wherein the third member is coupled to the second member by a second hinge.

21 Claims, 11 Drawing Sheets

(51) Int. Cl.
*B65D 25/10* (2006.01)
*B65D 43/16* (2006.01)
*A61M 5/00* (2006.01)
*A61J 1/20* (2006.01)

(52) U.S. Cl.
CPC ......... *B65D 21/0223* (2013.01); *B65D 25/10* (2013.01); *B65D 43/16* (2013.01); *B65D 43/162* (2013.01); *A61J 1/2096* (2013.01); *B65D 2543/00166* (2013.01); *B65D 2543/00296* (2013.01); *B65D 2543/00527* (2013.01); *B65D 2543/00537* (2013.01); *B65D 2543/00574* (2013.01); *B65D 2543/00648* (2013.01); *B65D 2543/00694* (2013.01); *B65D 2543/00731* (2013.01); *B65D 2543/00805* (2013.01); *B65D 2543/00944* (2013.01)

(58) Field of Classification Search
CPC ........ A61M 5/008; A61B 50/20; A61B 50/30; A61B 50/33
USPC ....... 206/438, 571, 570, 364, 365, 366, 363, 206/370
See application file for complete search history.

(56) References Cited

U.S. PATENT DOCUMENTS

| | | | |
|---|---|---|---|
| 1,995,799 A * | 3/1935 | Doniger | A61F 17/00 206/229 |
| 4,106,621 A | 8/1978 | Sorenson | |
| D261,234 S | 10/1981 | Abraham | |
| 4,671,408 A * | 6/1987 | Raines | A61M 5/002 206/1.5 |
| 4,848,587 A | 7/1989 | Nipp | |
| 4,921,096 A * | 5/1990 | McFarlane | A61M 25/002 206/349 |
| 4,976,370 A | 12/1990 | Cassel | |
| D313,502 S | 1/1991 | Vasky | |
| 5,511,684 A | 4/1996 | Weaver | |
| 5,566,828 A | 10/1996 | Claes et al. | |
| D385,787 S | 11/1997 | Takano et al. | |
| D433,331 S | 11/2000 | Denham et al. | |
| 6,423,037 B1 | 7/2002 | Hijikata et al. | |
| 6,439,276 B1 * | 8/2002 | Wood | A61M 5/1782 141/27 |
| 6,540,078 B1 | 4/2003 | Homent et al. | |
| D491,315 S | 6/2004 | Dittmer et al. | |
| D536,491 S | 2/2007 | Schumaier | |
| D548,070 S | 8/2007 | Swain | |
| D605,034 S | 12/2009 | Sarantis | |
| 7,731,678 B2 | 1/2010 | Tennican et al. | |
| 7,770,730 B2 | 8/2010 | Booker et al. | |
| 7,806,265 B2 | 10/2010 | Timm | |
| D694,102 S | 11/2013 | Bellamah et al. | |
| 8,910,781 B2 | 12/2014 | Pipes et al. | |
| D741,703 S | 10/2015 | Janson et al. | |
| 9,333,289 B1 * | 5/2016 | Hirschmann | A61M 5/002 |
| 9,649,428 B2 * | 5/2017 | Timm | A61M 5/002 |
| 2004/0182729 A1 | 9/2004 | Farrar et al. | |
| 2007/0251983 A1 | 11/2007 | Freeze | |
| 2008/0124954 A1 | 5/2008 | Wei Chen | |
| 2011/0306928 A1 * | 12/2011 | Duncan | A61M 5/1452 604/103.01 |
| 2012/0024855 A1 | 2/2012 | Smyers | |

FOREIGN PATENT DOCUMENTS

| | | |
|---|---|---|
| JP | D1179324 | 7/2003 |
| WO | WO 2007/091153 | 8/2007 |
| WO | WO2011/104711 A1 | 9/2011 |
| WO | 2011141871 A1 | 11/2011 |

OTHER PUBLICATIONS

International Search Report and the Written Opinion of the International Searching Authority for International Application No. PCT/US13/49322, ISA/US, dated Dec. 16, 2013, 10 pgs.

* cited by examiner

DEVICE CONTAINER

REFERENCE TO EARLIER FILED APPLICATIONS

This application is the national phase application of International Application No. PCT/US2013/049322, filed Jul. 3, 2013 and published as WO 2014/008397, which claims the benefit of U.S. Provisional Application No. 61/667,550, filed Jul. 3, 2012, both of which are incorporated herein by reference in their entireties.

FIELD OF THE INVENTION

The present invention generally relates to device containers. More particularly, embodiments of the present invention relate to containers for therapeutic kits having improved ergonomics, versatility, durability, and/or ease of use.

BACKGROUND OF THE INVENTION

Many people suffer from diseases or medical conditions that call for treatment by therapeutics. The preparation and administration of a therapeutic liquid to an individual often involves the mixing of two or more medicaments or other substances to form the therapeutic liquid and the subsequent delivery of the mixed therapeutic liquid to the individual. The mixing of medicaments or other substances often involves extraction of one medicament or other substance in liquid form from a vial or other vessel and transfer of this medicament or other substance into a separate vessel, such as a syringe, that holds the other medicament or substance.

Some therapeutics are sold to patients and caregivers as part of therapeutic "kits." These kits may include, for example, one or more vials, syringes, and the medicaments or substances that will form the therapeutic liquid, as well as a container for containing these components.

Existing therapeutic kit containers suffers from many shortcomings. For example, many existing therapeutic kit containers are unduly large and/or not sufficiently durable such that these containers are neither convenient nor safe to store or travel with. As a further example, many existing therapeutic kit containers are essentially empty vessels lacking ergonomic structure with no form of internal organization such that users may be required to dig or fumble around for the components they need at a given time. Finally, while many existing therapeutic kit containers are capable of merely storing their contents prior to use, these containers do not include structural features that may actually aid the user in therapeutic liquid preparation and administration.

What are needed are new therapeutic kit containers offering improved ergonomics, versatility, durability, and/or ease of use for patients and caregivers preparing and administering therapeutics.

It should be noted, however, that while the present discussion focuses primarily on therapeutic kit containers, some embodiments of the device containers described herein need not be limited to use with therapeutic kits, and may be suitable for storing items for a variety of non-therapeutic and non-medical purposes.

BRIEF SUMMARY OF THE INVENTION

Embodiments of the present invention may relate to a container having a closed configuration and an open configuration. The container may include a first member having an outer surface, a second member having an outer surface, wherein the second member is coupled to the first member by a first hinge, and a third member having an outer surface, wherein the third member is coupled to the second member by a second hinge, wherein the container is configured such that in the closed configuration, the outer surfaces of the first and third members are approximately parallel to one another and facing opposite from one another, and wherein the container is configured such that in the open configuration, the outer surfaces of the first, second, and third members are approximately parallel to one another and facing the same direction.

Embodiments of the present invention may also relate to a container having a closed configuration and an open configuration. The container may include a top panel, a side panel, wherein the side panel is configured to releasably hold a vial, and a bottom panel, wherein the container is configured such that in the closed configuration, the top and bottom panels are approximately parallel to one another, the side panel is approximately perpendicular to the top and bottom panels, and the side panel is configured to releasably hold a vial in such a way that a longitudinal axis of the vial would be approximately parallel to the top and bottom panels.

Embodiments of the present invention may further relate to a container that may include a first member configured to releasably hold a syringe barrel, a second member configured to releasably hold a vial, wherein the second member is coupled to the first member by a first hinge, and a third member configured to releasably hold a vial adapter, wherein the third member is coupled to the second member by a second hinge.

Embodiments of the present invention may also relate to a therapeutic kit that may include a syringe barrel, a vial having a cap and a base, and a container for holding syringe barrel and the vial, where the container may include a member configured to releasably hold the vial by its base, wherein the container is configured such that a user may couple the syringe barrel to the cap of the vial without first releasing the vial from the member.

Embodiments of the present invention may further relate to a therapeutic kit that may include a syringe barrel having a longitudinal axis, a vial having a longitudinal axis, and a container for holding the syringe barrel and the vial, wherein the container has closed configuration and an open configuration, where the container may include a first member configured to releasably hold the syringe barrel; a second member configured to releasably hold the vial, wherein the longitudinal axis of the syringe barrel is approximately parallel to the longitudinal axis of the vial when the container is in its closed position, and wherein the longitudinal axis of the syringe barrel is approximately perpendicular to the longitudinal axis of the vial when the container is in its open position.

Embodiments of the present invention may also relate to a therapeutic kit that may include a vial, a syringe barrel, and a container for holding the syringe barrel and the vial, where the container may include a member configured to releasably hold the vial in an upright position, wherein the container is configured to provide stability to the vial while the vial is releasably held in the upright position, and wherein the container is further configured to provide stability to the syringe barrel when the syringe barrel is coupled to the vial while the vial is still releasably held in the upright position.

In some embodiments of the present invention a container configured for releasably holding a syringe, vial, and vial adapter may itself be contained within a larger outer packaging container that may include labeling, marketing, or other product information on a surface of the outer packaging container.

In addition to a syringe, vial, and vial adapter, in further embodiments of the present invention, a therapeutic kit may include additional elements such as, for example, product instructions, an infusion needle set, alcohol swabs, gauze pads, or band-aids. Such additional elements may be included within the same container that holds the syringe, vial, and vial adapter, in a larger outer packaging container, or in an entirely different container that is included in the kit.

In other embodiments of the present invention, a single therapeutic kit may be configured to hold multiple syringes, multiple vials, and/or multiple vial adapters.

It should be noted that while the present discussion focuses primarily on therapeutic kit containers, some embodiments of the device containers described herein need not be limited to use with therapeutic kits, and may be suitable for storing items for a variety of non-therapeutic and non-medical purposes.

Further embodiments, features, and advantages of the present invention, as well as the structure and operation of the various embodiments of the present invention, are described in detail below with reference to the accompanying drawings.

BRIEF DESCRIPTION OF THE FIGURES

The accompanying drawings, which are incorporated herein and form a part of the specification, illustrate the present invention by way of example, and not by way of limitation, and, together with the description, further serve to explain the principles of the invention and to enable a person skilled in the pertinent art to make and use the invention.

DETAILED DESCRIPTION OF THE INVENTION

The present invention will now be described in detail with reference to embodiments thereof as illustrated in the accompanying drawings. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Many people suffer from diseases or medical conditions that call for treatment by therapeutics. As used herein, the term "therapeutic" refers to something pertaining to the treatment or curing of a disease or medical condition. Therapeutic treatments may involve, for example, medicaments, medical devices, or physical activities. As used herein, the term "medicament" refers to a substance for treating or curing a disease or medical condition.

Figure 1:
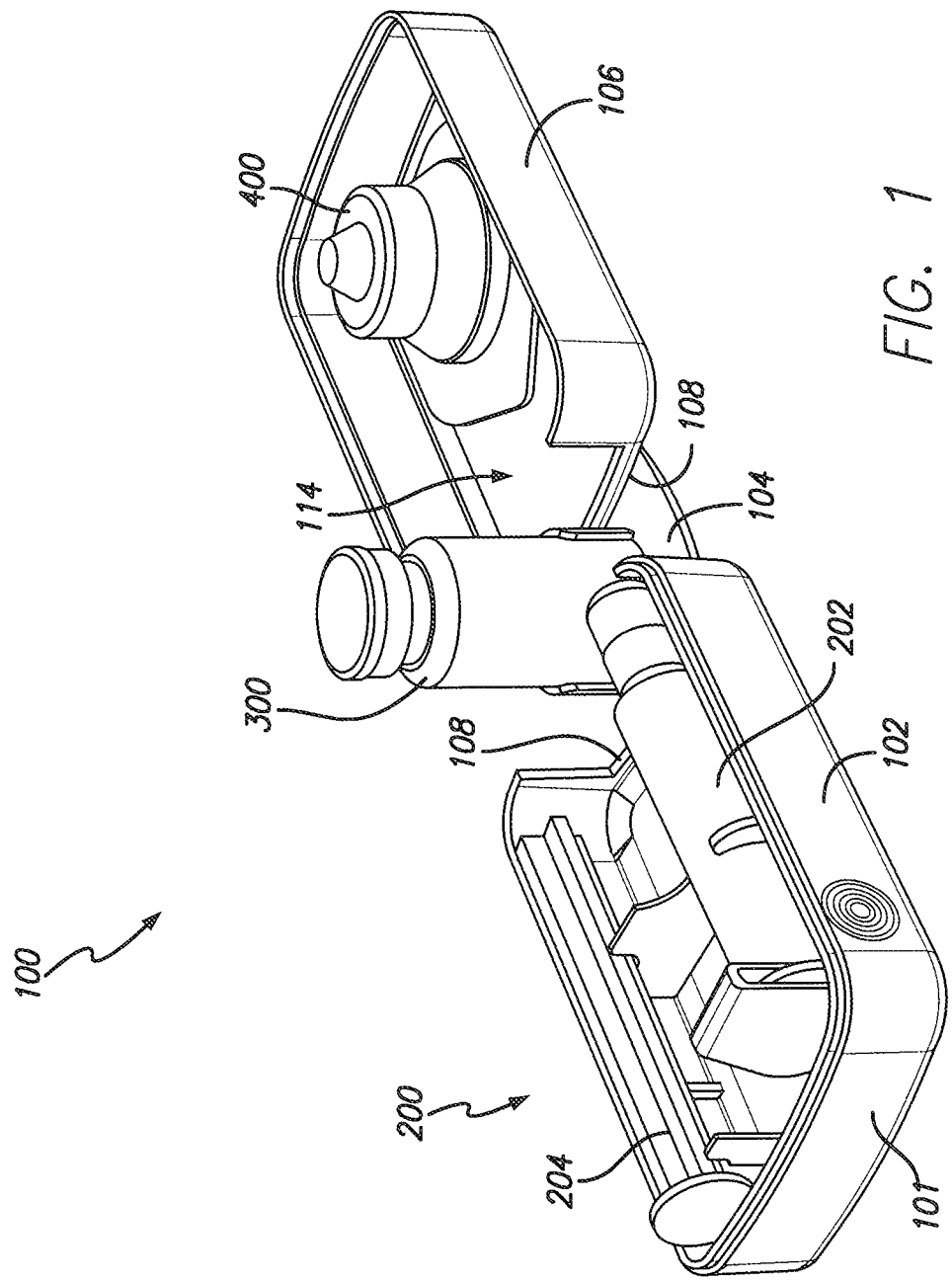
FIG. 1 is a front perspective view from above of a therapeutic kit container in an open configuration including various components according to an embodiment of the present invention.

Some therapeutics, such as medicaments or medical devices, may be sold to patients and caregivers as part of therapeutic "kits." FIG. 1 is a front perspective view from above of a therapeutic kit 100 container 101 in an open configuration including various components according to an embodiment of the present invention. Therapeutic kits 100 are useful to patients and caregivers because they may contain one or more medicaments, medical devices, and/or other components in a single package for use in administration of a therapy.

As illustrated in FIG. 1, a therapeutic kit 100 may include a container 101. A container 101 may be anything configured to contain objects or substances such as, for example, a carton, box, crate, can, or bottle. Containers 101 according to embodiments of the present invention may come in a variety of shapes and sizes, be made from a variety of materials, and have a variety of open and closed configurations.

In one embodiment of the present invention, as illustrated throughout the figures, the therapeutic kit 100 container 101 may be generally shaped like a rectangular prism with rounded edges in its closed configuration. In other embodiments, the container 101 may be generally shaped, for example, like a cube, a triangular prism, a cylinder a sphere, a cone, or a frustocone, with either straight or rounded edges. In some embodiments, rounded edges may desirable as they may present less risk of injury to sensitive patients.

The overall size of the container 101 in its closed configuration may vary depending on the size and shape of the medicaments, medical devices, and/or other components to be stored in the container. In one embodiment, the container 101 may be between 2.1 and 3.1 inches wide, between 3.5 and 4.5 inches long, and between 1.0 and 2.0 inches tall in its closed configuration. In another embodiment, the container 101 may be approximately 2.6 inches wide, approximately 4.0 inches long, and approximately 1.5 inches tall in its closed configuration. In some embodiments, the overall size of the container 101 in its closed configuration should be minimized as a smaller container 101 may be easier for a patient or caregiver to store or travel with, particularly if a plurality of containers 101 are to be stored or carried.

Therapeutic kit 100 containers 101 according to embodiments of the present invention may be made from a wide variety of materials including, for example, plastics such as polypropylene, polyvinylchloride, polytetrafluoroethylene, polyethersulfone, polyethylene, polyurethane, polyetherimide, polycarbonate, polyetheretherketone, polysulfone, cyclic olefin polymer, or cyclic olefin copolymer, cardboard, paper, metal, glass, wood, or combinations thereof. In some embodiments, forming the container 101 entirely from a plastic such as polypropylene may be desirable as the resulting container could be formed cost effectively by an injection molding process, and may be configured to be both structurally durable and waterproof.

In some embodiments of the present invention, the therapeutic kit 100 may also include a larger outer packaging container for containing the container 101. The larger outer packaging container may be used to store and secure the container 101 at various points in time during manufacture, distribution, sale, and/or use, and may include labeling, marketing, or other product information on a surface of the outer packaging container. The larger outer packaging container may be made from a wide variety of materials including, for example, plastics, cardboard, paper, metal, glass, wood, or combinations thereof.

Different containers 101 according to embodiments of the present invention may have a variety of open and closed configurations. In some embodiments, it may be desirable for the inside of a container 101 to be open to the outside environment at all times. In such embodiments, the container 101 may only have a single configuration whereby contents may be freely added or removed from the open container 101. In other embodiments, it may be desirable for the container to have discrete open and closed configurations, wherein the contents of the container 101 are not readily accessible from the outside environment in the closed configuration, but are readily accessible from the outside environment in the open configuration.

Figure 2:
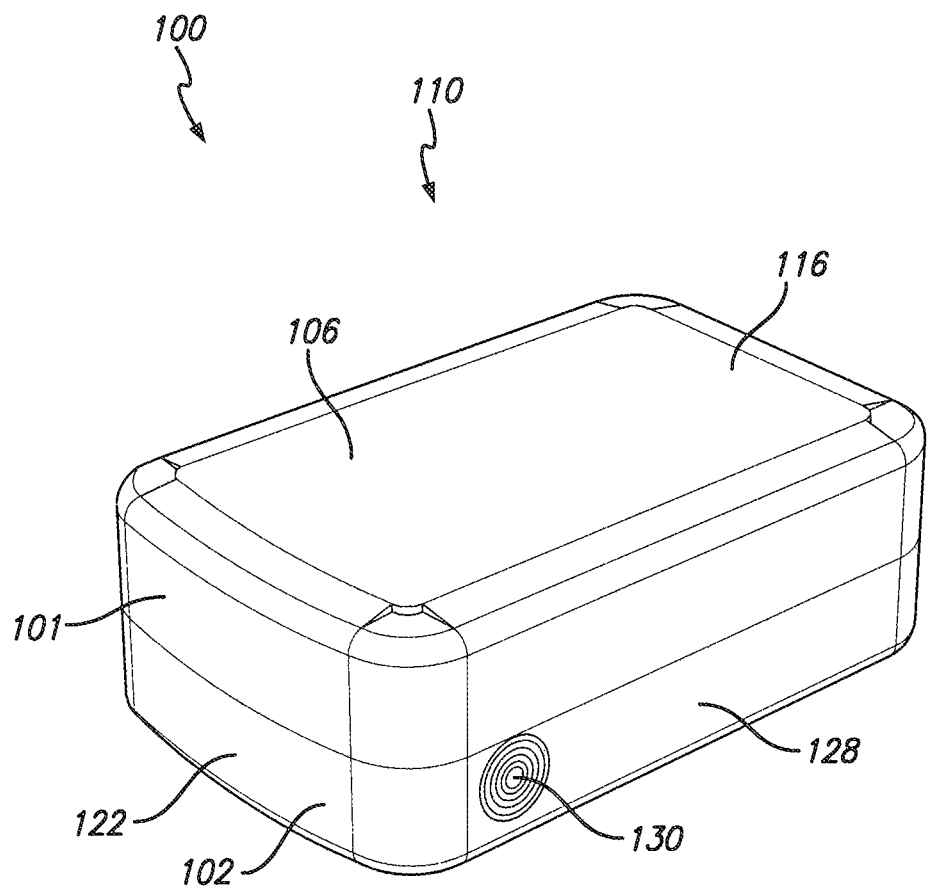
FIG. 2 is a front perspective view from above of a therapeutic kit container in a closed configuration according to an embodiment of the present invention

According to one embodiment of the present invention, FIG. 1 illustrates a therapeutic kit 100 container 101 (including various components) in an open configuration, while FIG. 2 illustrates the therapeutic kit 100 container 101 in a closed configuration. In both configurations, the container, or portions thereof, may form one or more interior cavities 114 within the container 101.

The container 101 illustrated in FIG. 1 can be considered to be made up of a plurality of members. These members include a first member 102, a second member 104, and a third member 106. In other embodiments, the container 101 may be made up of less than or greater than three members. The first member 102 and the third member 106 illustrated in FIG. 1 include relatively large flat panels and upwardly projecting sidewalls, while the second member 104 more closely resembles a smaller flat panel without upwardly projecting sidewalls.

The first member 102, second member 104, and third member 106 may be joined together by one or more hinges 108. For the container 101 illustrated in FIG. 1, the first member 102 is joined to the second member 104 by a first hinge 108, and the second member 104 is joined to the third member 106 by a second hinge 108. Hinges 108 may be, for example, living hinges, butt hinges, flush hinges, barrel hinges, concealed hinges, or piano hinges. In some embodiments, one or more hinges may not be present and members of the container 101 may be completely separable from one another. In an embodiment where the container 101 is formed from a plastic by an injection molding process, living hinges 108 connecting various members may be formed during the injection molding process.

Therapeutic kit 100 containers 101 according to embodiments of the present invention may contain one or more medicaments, medical devices, and/or other components for use in administration of a therapy. With reference to FIG. 1, in one embodiment, a container 100 may be configured to store a syringe 200, a vial 300, and a vial adapter 400. The syringe 200 may optionally be separated into syringe 200 barrel 202 and syringe 200 plunger rod 204 components while in storage in the container 100. In other embodiments, the container 101 may be configured to store less or more components than those specified above, or configured to store entirely different components.

Some therapeutic treatments involve the preparation and administration of a therapeutic liquid to a patient, which may involve the mixing of two or more medicaments or other substances to form the therapeutic liquid. The mixing of medicaments or other substances often involves extraction of one medicament or substance in liquid form from a vial 300 or other vessel and transfer of this medicament substance into a separate vessel (such as a syringe 200 barrel 202) that holds the other medicament or substance. Accordingly, therapeutic kits 100 including containers 101, such as those described herein with respect to embodiments of the present invention, may offer improved ergonomics, versatility, durability, and/or ease of use for patients and caregivers preparing and administering therapeutics.

Returning to a discussion of the configuration of the container 101 itself, FIG. 2 is a front perspective view from above of a therapeutic kit 100 container 101 in a closed configuration according to an embodiment of the present invention. Because the container 101 is illustrated here in a closed configuration, only the outer surface 110 of the container 101 can be seen in this figure. As illustrated, the first member 102 is located on the bottom half of the container 101 in the closed configuration. This is the same first member 102 that was illustrated as being on the left side of FIG. 1. The third member 106 is located on the top half of the container 101 in the closed configuration, as illustrated in FIG. 2. This is the same third member 106 that was illustrated as being on the right side of FIG. 1. Because FIG. 2 is a front perspective view from above of a therapeutic kit 100 container 101 in a closed configuration, neither the second member 104 nor any hinges 108 are visible from this view.

As illustrated in FIG. 2, in one embodiment, the container 101 may be considered to have a front side 122 and a right side 128 that are visible in this view. A rear side 124 and a left side 126 are not visible in this view. In addition, the container 101 may be considered to have a top panel 116, which is a relatively large, flat panel forming part of the outer surface 110 of the third member 106. In some embodiments, the container 101 may also include a release element 130 that may aid in transitioning the container 101 from a closed configuration to an open configuration, as described in further detail below. In FIG. 2, a single release element 130 is illustrated on the right side 128 of the container 101. In some embodiments, the release element 130 may be located elsewhere, or multiple release elements 130 may be present.

Figure 3A:
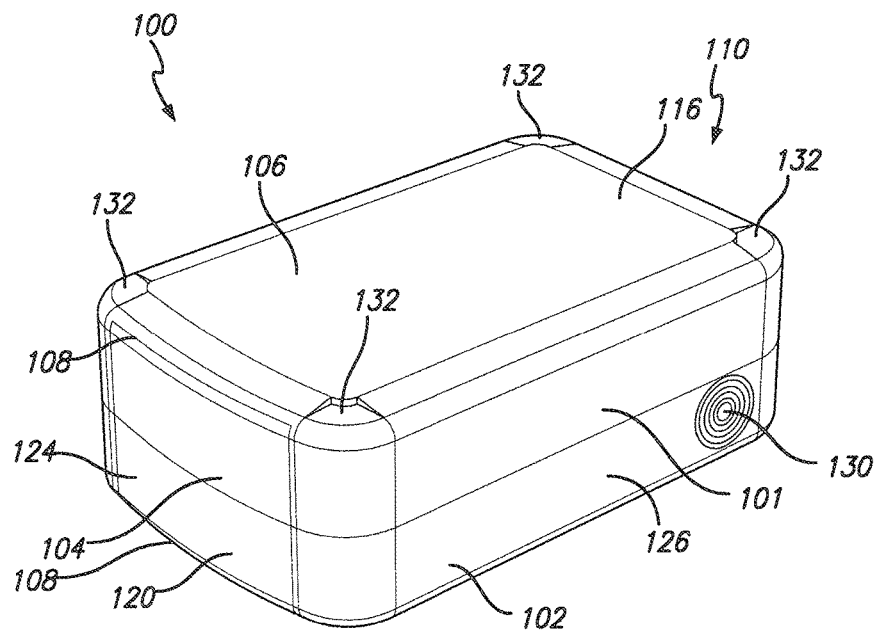
FIG. 3A is a rear perspective view from above of a therapeutic kit container in a closed configuration according to an embodiment of the present invention

FIG. 3A is a rear perspective view from above of the therapeutic kit 100 container 101 in a closed configuration according to an embodiment of the present invention. Because the container 101 is illustrated here in a closed configuration, only the outer surface 110 of the container 101 can be seen in this figure. As illustrated, the first member 102 is located on the bottom half of the container 101 in the closed configuration. This is the same first member 102 that was illustrated as being on the bottom half of the container 101 in FIG. 2, but from a different angle. The third member 106 is located on the top half of the container 101 in the closed configuration, as illustrated in FIG. 3A. This is the same third member 106 that was illustrated as being on the top half of the container 101 in FIG. 2. Because FIG. 3A is a rear perspective view from above of a therapeutic kit 100 container 101 in a closed configuration, both the second member 104 and two discrete hinges 108 are visible from this view.

As illustrated in FIG. 3A, in one embodiment, the container 101 may be considered to have a rear side 124 and a left side 126 that are visible in this view. A front side 122 and a right side 128 are not visible in this view. In addition, the top panel 116 of the container 101 that was illustrated in FIG. 2 is also visible here in FIG. 3, but from a different angle. The top panel 116 is a relatively large, flat panel forming part of the outer surface 110 of the third member 106. In addition to the release element 130 on the right side 128 of the container 101 illustrated in FIG. 2, in some embodiments, the container 101 may also include a release element 130 on its left side 126 as illustrated in FIG. 3A. The release elements 130 may aid in transitioning the container 101 from a closed configuration to a closed configuration, as described in further detail below.

Figure 11:
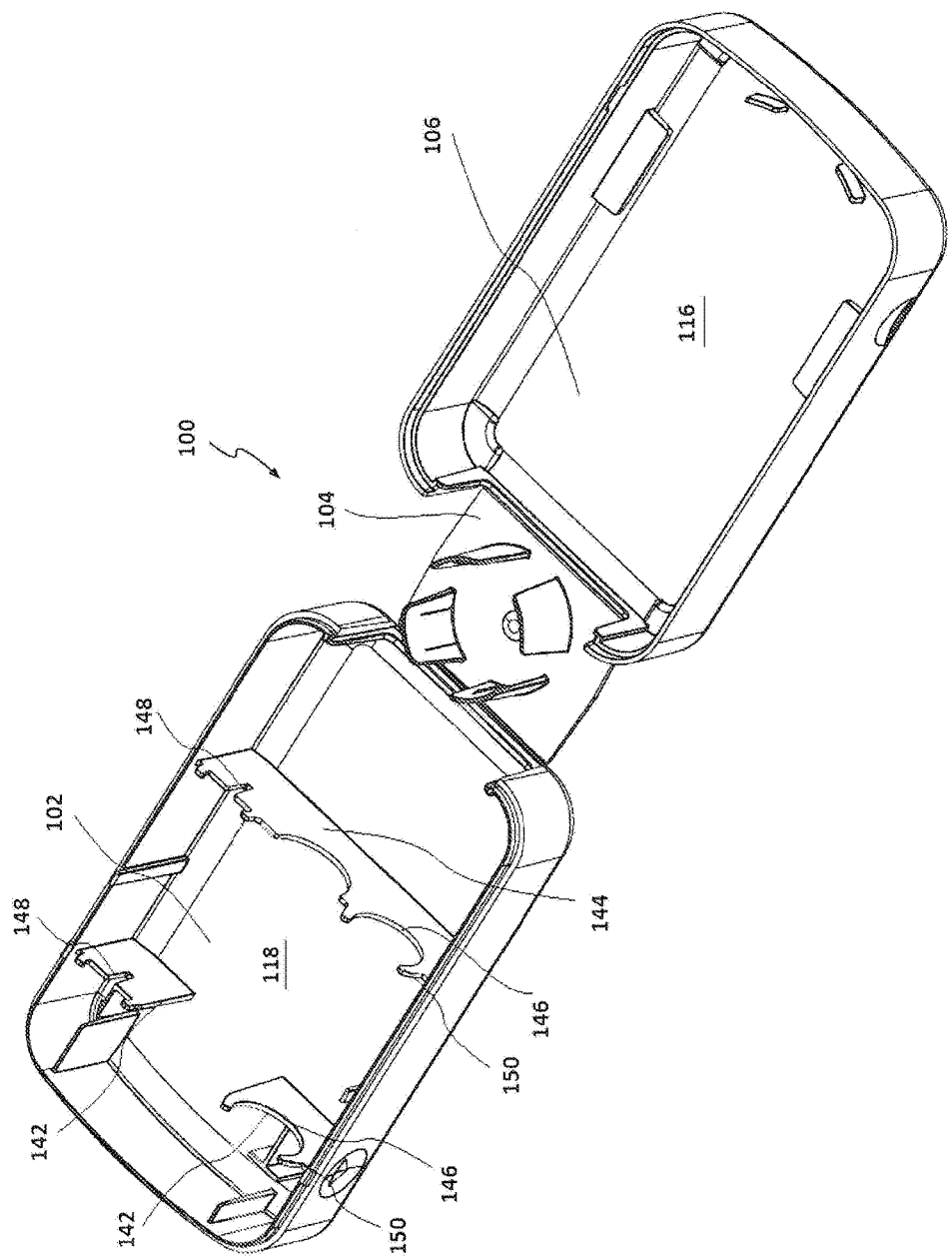
FIG. 11 is a rear perspective view from above of an empty therapeutic kit container in an open configuration according to an embodiment of the present invention.

Although the release elements 130 are illustrated in FIG. 2 and FIG. 3A as being located on the first member 102 of the container 101, on other embodiments, one or more release elements 130 may instead be located on the second member 104 or the third member 106 of the container 101. In some embodiments, the container 101 may include release elements 130 on both the first member 102 and the third member 106 that are vertically aligned with one another. Another embodiment may include release elements 130 as depicted in FIG. 11.

It should also be noted that, in an embodiment, as illustrated in FIG. 3A, the container 101 may include one or more mating elements for mating with other containers 101 that are stacked on top of or below the container 101. For example, as illustrated in FIG. 3A, the container 101 may include a plurality of top mating elements 132 on the outer surface 110 of the third member 106. In an embodiment, the top mating elements 132 may be upward facing depressions located at or near the corners of the third member 106. As explained in further detail below, the top mating elements 132 of one container 101 may mate with complementary elements of another container 101 to allow multiple containers 101 to be conveniently and securely stacked for storage or travel.

Figure 3B:
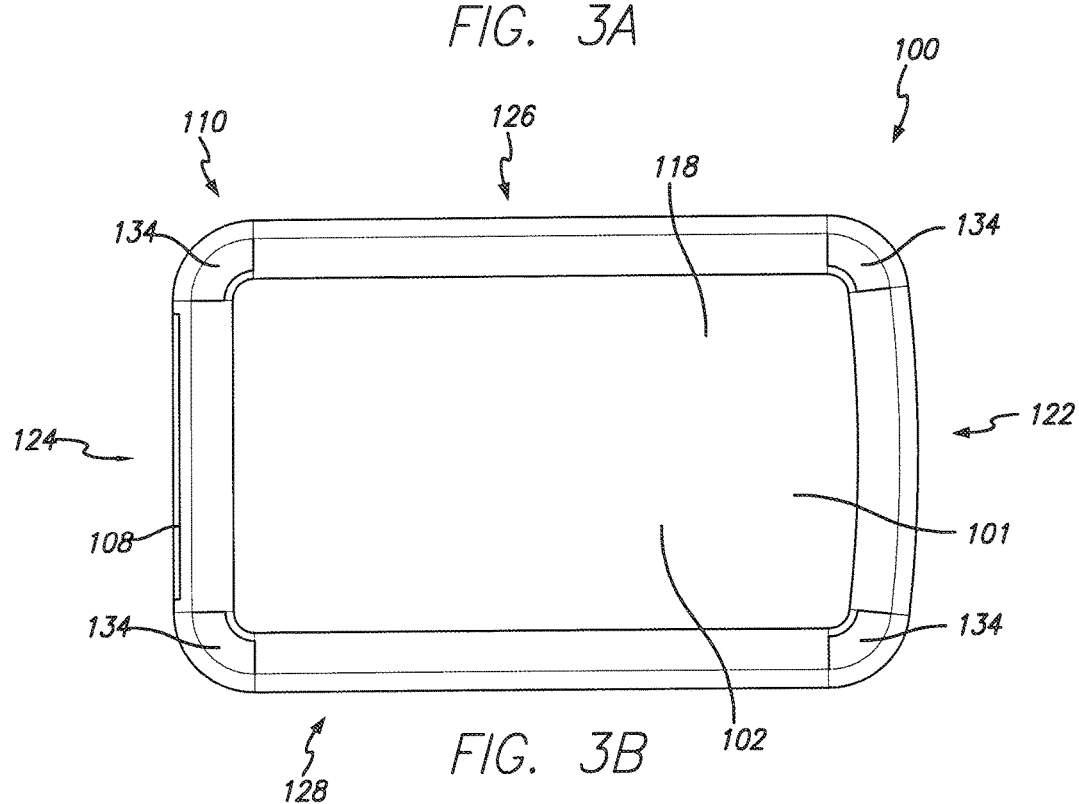
FIG. 3B is a bottom view of a therapeutic kit container in a closed configuration according to an embodiment of the present invention

FIG. 3B is a bottom view of the therapeutic kit 100 container 101 in a closed configuration according to an embodiment of the present invention. Because the container 101 is illustrated here in a closed configuration, only the outer surface 110 of the container 101 can be seen in this figure. As illustrated, the first member 102 is located on the bottom of the container 101 in the closed configuration. This is the same first member 102 that was illustrated as being on the bottom half of the container 101 in FIG. 3A, but from a different angle. Because FIG. 3B is a bottom view of a therapeutic kit 100 container 101 in a closed configuration, both the second member 104 and the third member 106 are not visible from this view. A hinge 108, which happens to be a living hinge 108, is visible from this view.

As illustrated in FIG. 3B, in one embodiment, the container 101 may be considered to have a bottom panel 118, which is a relatively large, flat panel forming part of the outer surface 110 of the first member 102. It should also be noted that, in an embodiment, as illustrated in FIG. 3B, the container 101 may include one or more mating elements for mating with other containers 101 that are stacked on top of or below the container 101. For example, as illustrated in FIG. 3B, the container 101 may include a plurality of bottom mating elements 134 on the outer surface 110 of the first member 102. In an embodiment, the bottom mating elements 134 may be downward facing extensions located at or near the corners of the first member 102. As explained in further detail below, these bottom mating elements 134 of one container 101 may mate with complementary top mating elements 132 of another container 101, as described above with respect to FIG. 3A, to allow multiple containers 101 to be conveniently and securely stacked for storage or travel.

In some embodiments, mating elements, such as top mating elements 132 and bottom mating elements 134, may not be present in the container 101. In other embodiments, the mating elements may take on substantially different mating configurations beyond depressions and extensions, or the positions of the depressions and extensions may be swapped.

Figure 4:
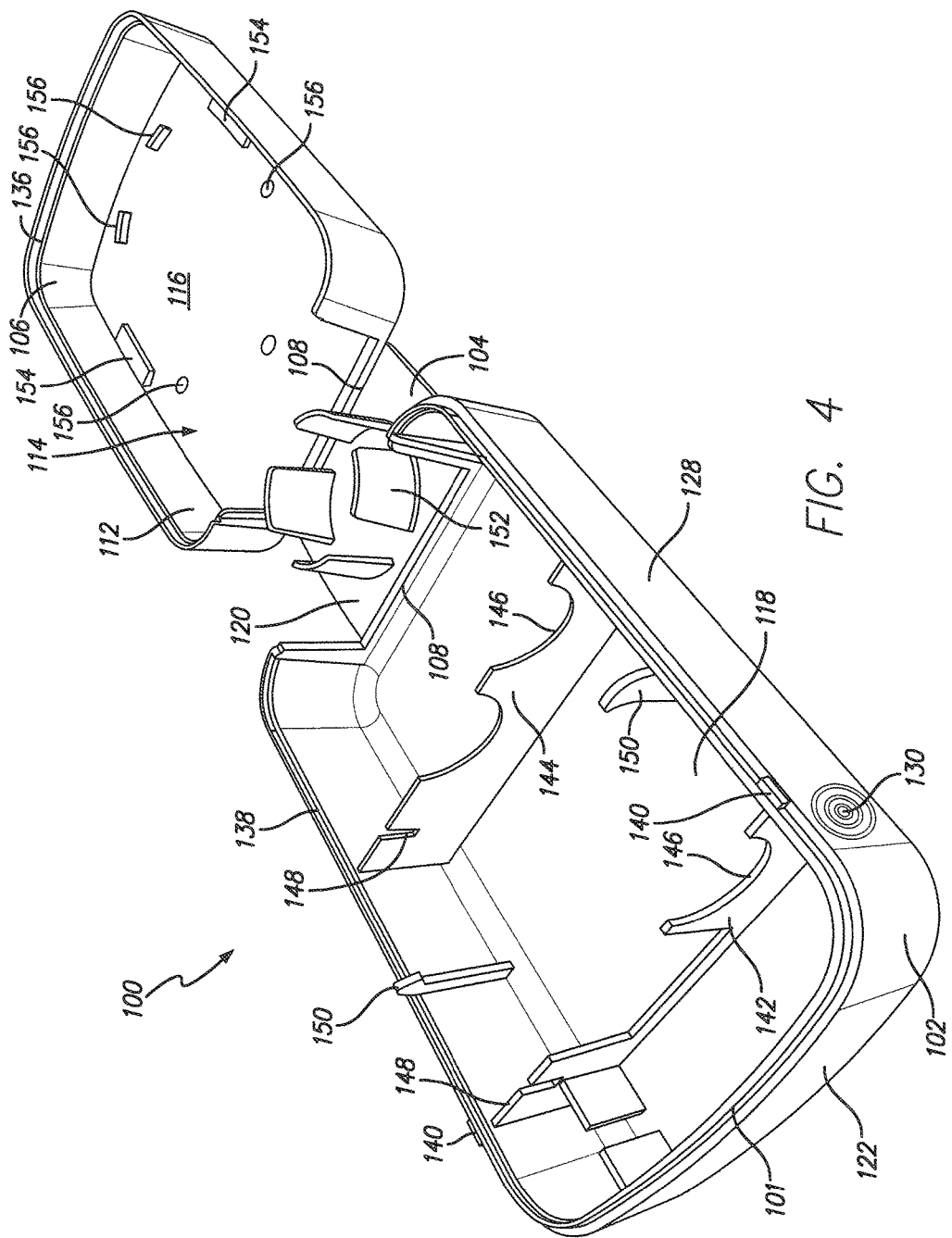
FIG. 4 is a front perspective view from above of an empty therapeutic kit container in an open configuration according to pan embodiment of the present invention.

Returning to a discussion of the inner surface 112 of the container 101, FIG. 4 is a front perspective view from above of an empty therapeutic kit 100 container 101 in an open configuration according to an embodiment of the present invention. In this illustration, the syringe 200, vial 300, and vial adapter 400 have been removed from the container 101.

As illustrated in FIG. 4, in one embodiment, the first member 102 may include several structural features that are designed to releasably hold a syringe 200 in the container 101. For example, on the inner surface 112 of the container 101, the first member 102 may include one or more support walls. Support walls may be upwardly extending walls configured to releasably mate with the syringe 200 or components thereof.

In one embodiment, on the inner surface 112 of the container 101, the first member 102 may include a first support wall 142 and a second support wall 144. The first support wall 142 may extend upwardly from the inner surface 112 of the first member 102 of the container 101, and may run from the left side 126 of the container to the right side 128 of the container. In other embodiments, the first support wall 142 may be oriented with respect to the first member 102 in a different fashion, or may not run all the way across the container 101 from one side to another. In an embodiment, the wall may consist of two or more discrete walls. In still other embodiments, instead of a "wall," the supporting structure may be a block, sphere, or other suitable shaped support structure.

In one embodiment, the first support wall 142 may include certain structural features that may to allow it to releasably mate with the syringe 200 or components thereof. For example, in FIG. 4, the first support wall 142 includes an arcuate depression 146 and a groove 148. In other embodiments, the first support wall 142 may include additional arcuate depressions 146 and/or grooves 148, may not include these features, or may include additional structural features to allow the first support wall 142 to releasably mate with the syringe 200 or components thereof.

The arcuate depression 146 may be a semi-circular void in the otherwise continuous structure of the first support wall 142 that may be configured to releasably mate with a syringe 200 barrel 202. In embodiments where the syringe 200 barrel 202 is not cylindrical, a depression that is shaped differently than the arcuate depression 146 may be more appropriate. The size and shape of the depression may be varied according to the syringe 200 barrel 202.

The groove 148 may be a slit, thin rectangular carve out, thin triangular carve out, or other suitable void in the otherwise continuous structure of the first support wall 142 that may be configured to releasably mate with a syringe 200 plunger rod 204 where the plunger rod 204 is stored separately from the barrel 202. Grooves 148 may be appropriate in embodiments where the syringe 200 plunger rod 204 has a "X" shaped cross section formed from four equally spaced support beams, so that one of the beams may extend downward into a groove 148. In embodiments where the syringe 200 plunger rod 204 does not have an "X" shaped cross section, a groove 148 that is shaped differently than that depicted in FIG. 4 may be more appropriate. The size and shape of the groove 148 may be varied according to the syringe 200 plunger rod 204.

In one embodiment, in addition to the first support wall 142, the inner surface 112 of the first member 102 of the container 101 may also include a second support wall 144. The second support wall 144 may extend upwardly from the inner surface 112 of the first member 102 of the container 101, and may run from the left side 126 of the container to the right side 128 of the container. In other embodiments, the second support wall 144 may be oriented with respect to the first member 102 in a different fashion. In an embodiment, the first support wall 142 may be located closer to the front side 122 of the container 101, while the second support wall 144 may be located closer to the rear side 124 of the container 101.

In one embodiment, the second support wall 144 may include certain structural features that may to allow it to releasably mate with the syringe 200 or components thereof, and possibly the vial 300 or portions thereof. For example, in FIG. 4, the second support wall 144 includes an arcuate depression 146 and a groove 148. In other embodiments, the second support wall 144 may include additional arcuate depressions 146 and/or grooves 148, may not include these features, or may include additional structural features to allow the second support wall 144 to releasably mate with the syringe 200 or components thereof. In an embodiment, the second support wall 144 may include an arcuate depression 146 designed to conform to the shape of the vial 300 when the container 101 is in its closed configuration and the vial 300 and the second support wall 144 of the first member 102 are brought into proximity with one another.

As with the arcuate depression 146 described with respect to the first support wall 142, the arcuate depression 146 of the second support wall 144 may be a semi-circular void in the otherwise continuous structure of the second support wall 144 that may be configured to releasably mate with a syringe 200 barrel 202. In embodiments where the syringe 200 barrel 202 is not cylindrical, a depression that is shaped differently than the arcuate depression 146 may be more appropriate. The size and shape of the depression may be varied according to the syringe 200 barrel 202.

As with the groove 148 described with respect to the first support wall 142, the groove 148 of the second support wall 144 may be a slit, thin rectangular carve out, thin triangular carve out, or other suitable void in the otherwise continuous structure of the second support wall 144 that may be configured to releasably mate with a syringe 200 plunger rod 204 where the plunger rod 204 is stored separately from the barrel 202. Grooves 148 may be appropriate in embodiments where the syringe 200 plunger rod 204 has a "X" shaped cross section formed from four equally spaced support beams, so that one of the beams may extend downward into a groove 148. In embodiments where the syringe 200 plunger rod 204 does not have an "X" shaped cross section, a groove 148 that is shaped differently than that depicted in FIG. 4 may be more appropriate. The size and shape of the groove 148 may be varied according to the syringe 200 plunger rod 204.

In an embodiment of the present invention, the arcuate depressions 146 and/or grooves 148 of the first support wall 142 and the second support wall 144 may be aligned with one another so that the first member 102 may hold the syringe 200 barrel 202 and the syringe 200 plunger rod 204 in a way that efficiently uses space within the container 101.

In some embodiments, first support wall 142 and/or second support wall 144 may include, in addition to grooves 148, one or more other suitable voids. For example, FIG. 11 depicts an embodiment where an additional void or groove shaped and arranged perpendicular to the first groove 148 such that a syringe 200 plunger rod 204 having an "X" shaped cross section formed from four equally spaced support beams could be place into and/or held by the first support wall 142 and/or second support wall 144 material forming the additional void or groove. In some embodiments, the first support wall 142 and/or second support wall 144 may include structural features that are designed to releasably hold the syringe 200 plunger rod 204 in the container 101, such as one or more hooks 150.

In other embodiments, the first support wall 142 and/or second support wall 144 may include structural features that are designed to releasably hold the syringe 200 barrel 202 in the container 101, such as one or more hooks 150 that may be incorporated in to the arcuate depressions 146, as illustrated in FIG. 11.

In one embodiment, as illustrated in FIG. 4, the first member 102 may include several additional structural features that are designed to releasably hold the syringe 200 in the container 101. For example, on the inner surface 112 of the container 101, the first member 102 may also include one or more hooks 150. Hooks 150 may be curved, bulbous, or otherwise shaped extensions of or additions to the first member 102 that are configured to releasably mate with the syringe 200 or components thereof.

In one embodiment, on the inner surface 112 of the container 101, the first member 102 may include a first support wall 142 and a second support wall 144. The first support wall 142 may one hook 150 for mating with the syringe 200 barrel 202 and another hook 150 for mating with the syringe 200 plunger rod 204. As will be described in further detail below, the first support wall 142 and the second support wall 144 may work in concert with these hooks 150 such that the syringe 200 barrel 202 and the syringe 200 plunger rod 204 may be releasably placed in and removed from the container 101 by friction fitting.

In other embodiments, hooks 150 may include hinges, springs, or other structural features that may aid in their ability to releasably hold the syringe 200. In still other embodiments, hinges, springs, or other structural features may exist in the absence of hooks 150.

In some embodiments, discrete hooks 150 may not be present. Instead, as shown in FIG. 11, the first support wall 142 and/or second support wall 144 may include structural features that are designed to releasably hold the syringe 200 barrel 202 and/or plunger rod 204 in the container 101 that are directly be incorporated in to the arcuate depressions 146, but are not discrete separate hooks 150.

With further reference to FIG. 4, in other embodiments, the second member 104 may include structural features that are designed to releasably hold a vial 300 or other vessel in the container 101. For example, on the inner surface 112 of the container 101, the second member 104 may include a sleeve 152 or other structure for releasably mating with the vial 300 or components thereof.

In various embodiments, the inner surface 112 of the second member 104 may be configured to hold the vial 300 in a variety of different orientations. For example, as illustrated in FIG. 4, the second member 104 may include a cylindrical sleeve 152 that may be suited to releasably hold a generally cylindrically shaped vial 300. A cylindrical shaped sleeve 152 may be best suited to releasably hold a vial by its cap 302 or base 304, as these structures may fit matingly within a cylindrical shaped sleeve 152. In other embodiments, a sleeve 152 may take on other shapes as necessary to hold a vial 300 on its side.

In embodiments where the vial 300 is not cylindrical, a sleeve 152 that is shaped differently than the sleeve 152 of FIG. 4 may be more appropriate. The size and shape of the sleeve 152 may be varied according to the vial 300. Additionally, means other than sleeves 152 may be used to secure a vial in other embodiments. For example, adhesives, hook and look fasteners, snaps, slots, or other means may be used.

In the embodiment depicted in FIG. 4, the sleeve 152 includes four upwardly extending walls equally spaced apart and defining four equally spaced apart voids. The sleeve 152 may form a generally cylindrical, generally frustoconial, or other appropriate shape. In some embodiments, the sleeve 152 may include fewer or greater than three upwardly extending walls and voids. The sleeve 152 may be centered on the inner surface 112 of the second member 104, or it may be offset from center.

With further reference to FIG. 4, in other embodiments, the third member 106 may include structural features that are designed to releasably hold a vial adapter 400 in the container 101. In some embodiments, the vial adapter 400 may have a skirt 404 at its base. Accordingly, on the inner surface 112 of the container 101, the third member 106 may include one or more slots 154 and/or guides 156 for interfacing with the vial adapter 400 skirt 404.

As depicted in FIG. 4, slots 154 may consist of relatively short rails or tabs extending from the bottom and/or sides walls of the third member 106. As explained in further detail below in reference to other figures, it may be possible to slide or bend and insert the skirt 404 of a vial adapter 400, or portions thereof, under one or more slots 154 to releasably secure the vial adapter 400 to the container 101. FIG. 4 depicts one slot 154 extending from the left side 126 sidewall of the third member 106, and one slot 154 extending from the right side 128 of the bottom of the third member 106. In other embodiments, fewer or greater than two slots 154 may be employed, or slots may be entirely omitted.

As further depicted in FIG. 4, guides 156 may consist of relatively small bumps extending upward from the bottom surface of the third member 106. As explained in further detail below in reference to other figures, it may be possible to slide or bend and insert the skirt 404 of a vial adapter 400, or portions thereof, past or over one or more guides 156 to, in combination with one or more slots 154, releasably secure the vial adapter 400 to the container 101. FIG. 4 depicts one guide 156 bump extending from the bottom surface of the third member 106 toward the left side 126 of the third member 106, and another guide 156 bump extending from the bottom surface of the third member 106 toward the right side 128 of the third member 106. In other embodiments, fewer or greater than two guides 156 may be employed, or guides 156 may be entirely omitted. In some embodiments, guides 156 may take on other configurations beyond small bumps.

FIG. 4 also illustrates exemplary components of the container 101 that may aid in transitioning the container 101 from an open configuration to a closed configuration, and vice versa.

In one embodiment, a continuous two-step rim 138 runs across the upper edge of the sidewalls of the first member 102 of the container 101. In the illustrated embodiment, there is a discontinuity in this bottom rim 138 at the point where there is also a discontinuity in the sidewall due to the need to accommodate the second member 104 when the container 101 is in its closed configuration.

In addition, there may be a complimentary continuous two-step rim 136 that runs across the upper edge of the sidewalls of the third member 106 of the container 101. In the illustrated embodiment, there is a discontinuity in this top rim 136 at the point where there is also a discontinuity in the sidewall due to the need to accommodate the second member 104 when the container 101 is in its closed configuration.

The bottom rim 138 and the top rim 136 may matingly connect when the container 101 is transitioned to its closed configuration. In this configuration the two-step arrangement of one rim will meet with an opposite two-step arrangement of the other rim to create a closed seal.

In some embodiments of the present invention, this closed seal may be locked from unintended opening by way of one or more closure elements 140. Closure elements 140 may be any suitable locking means of various levels of complexity. In one embodiment, as illustrated in FIG. 4 the closure elements 140 may consist of a snap-fit elements. A snap-fit is a mechanical joint system where part-to-part attachment may be accomplished with locking features that are homogenous with one or the other of the components being joined. Joining requires the flexible locking features to move aside for engagement with the mating part, followed by return of the locking feature toward its original position to accomplish the interference required to latch the components together.

In one embodiment, the snap-fit closure elements 140 may include one or more locking protrusions on the bottom rim 138 of the first member 102, and corresponding mating locking indentations on the top rim 136 of the third member 106. When the container 101 is manipulated from its open configuration to its closed configuration, the top rim 136 of the third member 106 may be urged toward the bottom rim 138 of the first member 102 in such a way that the locking indentations on the top rim 136 slide over the locking protrusions on the bottom rim 138 thus locking the third member 106 in place against the first member 102.

In some embodiments, the container 101 may also include a release element 130 that may aid in transitioning the container 101 from a closed configuration to a closed configuration, such as the release elements 130 depicted in FIG. 2 and FIG. 3A. More specifically, the left side 126 and the right side 128 of the first member 102 may each have a release element 130 in the shape of a spherical dimple located just below the locking protrusions on the bottom rim 138 on the outer surface 110 of the container 101. An exemplary release element 130 can be seen in FIG. 4. To release the locking mechanism, a user may apply pressure to the one or more release elements 130 which may cause the side walls and the bottom rim 138 of the first member 102 to flex inward slightly. This inward flexion may result in the locking protrusions on the bottom rim 138 being pulled out of a locking configuration with the locking indentations on the top rim 136. Accordingly, the first member 102 and the third member 106 may be released from one another, the container 101 may be manipulated to an open configuration.

In other embodiments, other types of locking mechanisms employing alternate closure elements 140 and release elements 130 may be employed. In some embodiments less than or greater than two sets of closure elements 140 and release elements 130 may be employed, and in some embodiments closure elements 140 and release elements 130 may not be used at all.

Figure 5:
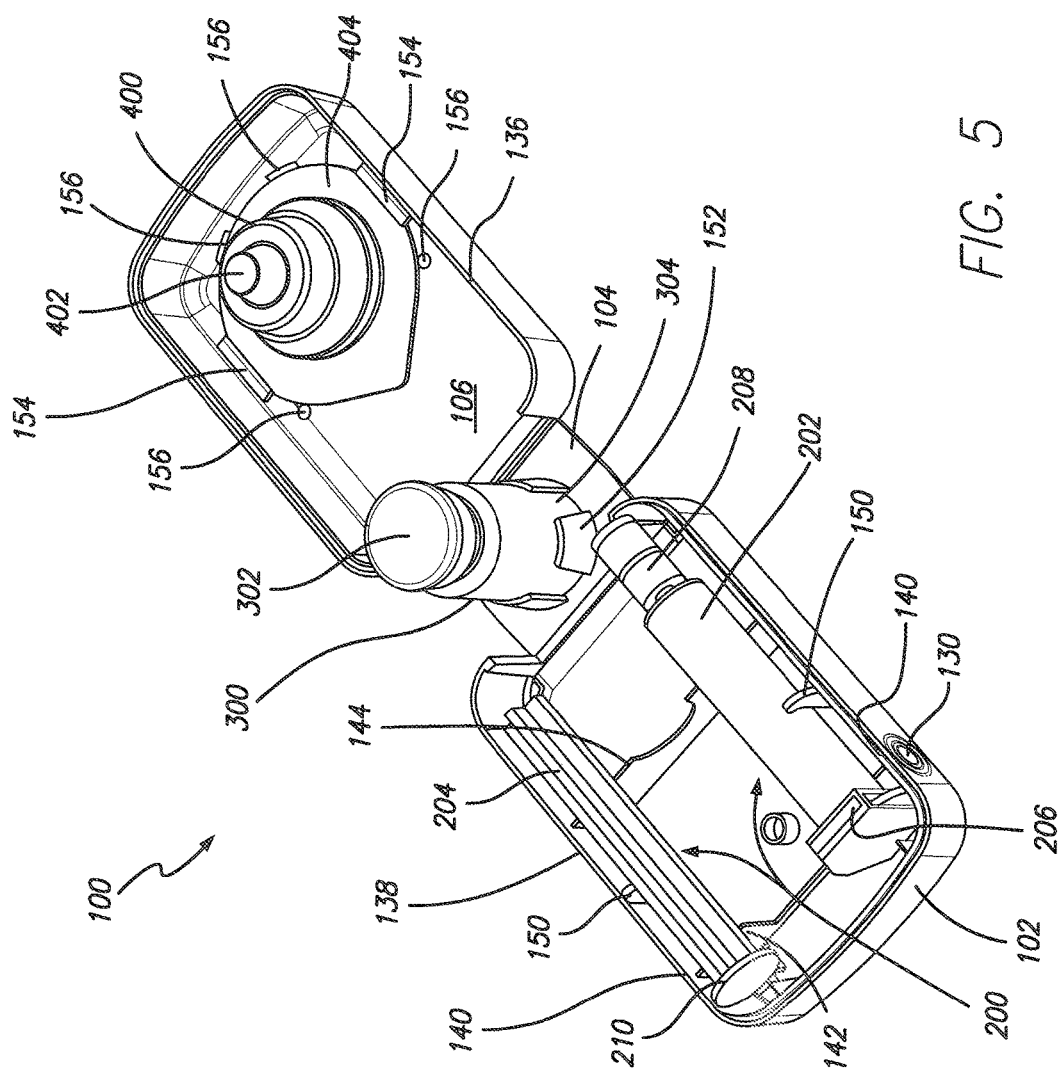
FIG. 5 is a front perspective view from above of a therapeutic kit container in an open configuration including various components according to an embodiment of the present invention.
Figure 6:
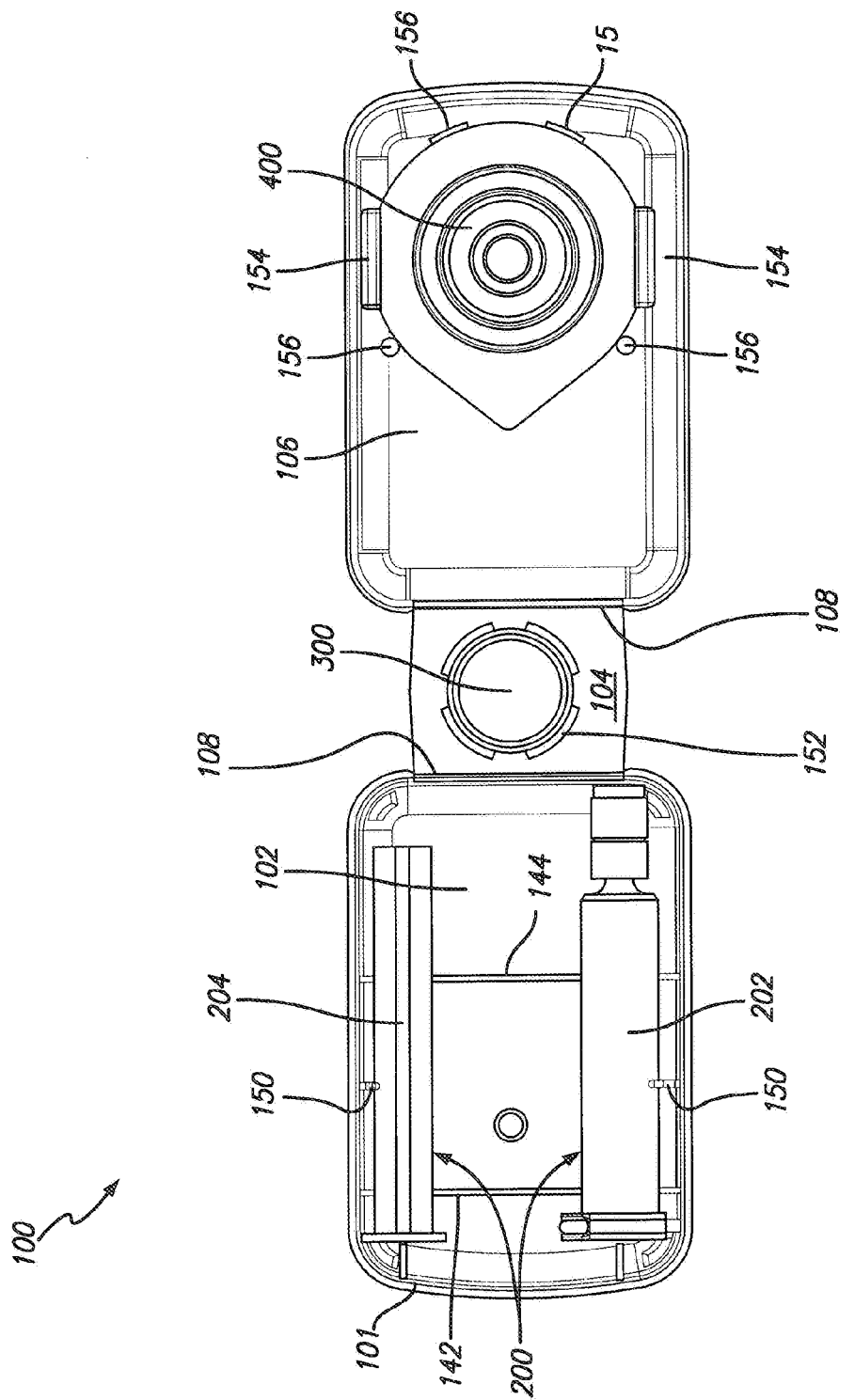
FIG. 6 is a top view of a therapeutic kit container in an open configuration including various components according to an embodiment of the present invention.
Figure 7:
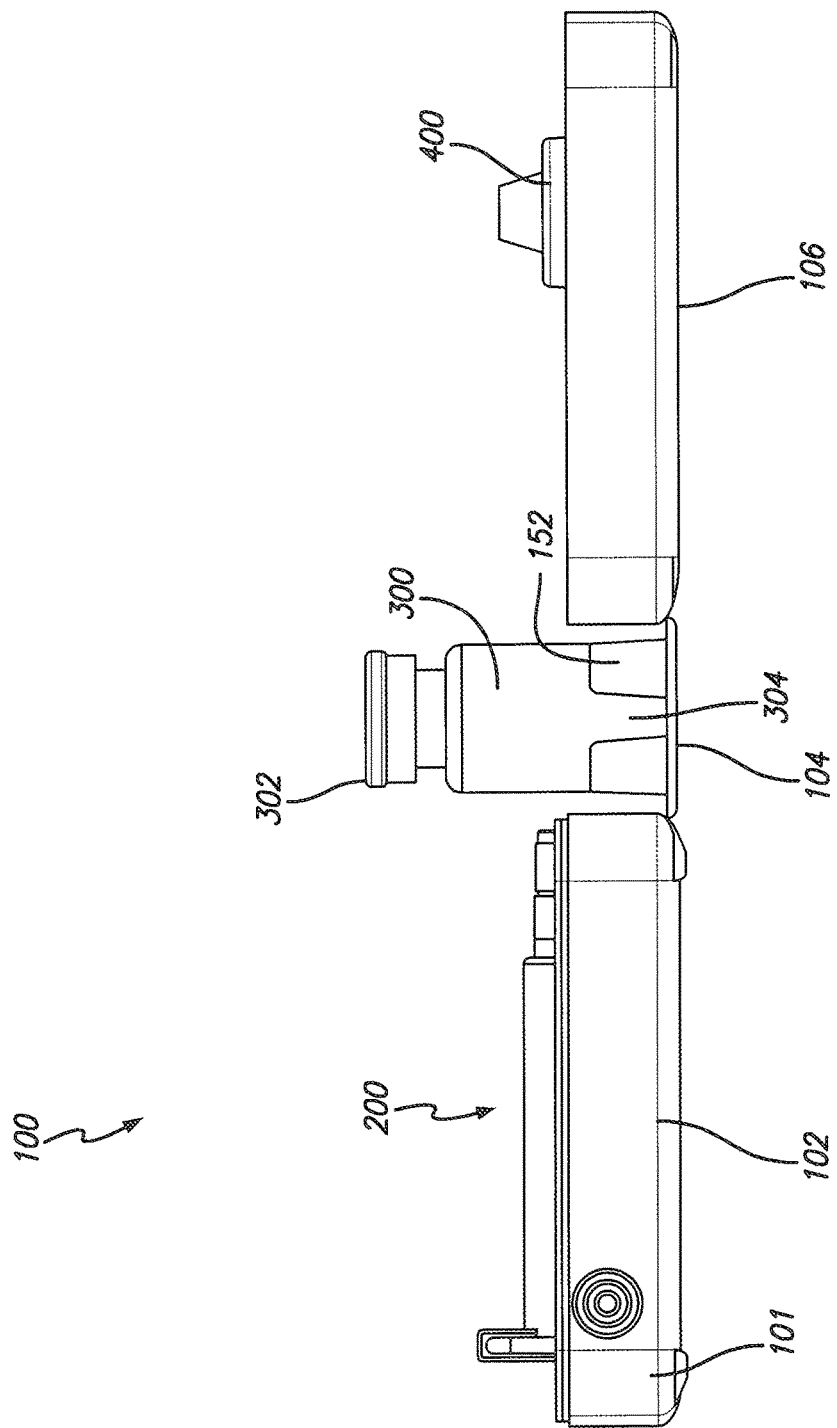
FIG. 7 is a right side view of a therapeutic kit container in an open configuration including various components according to an embodiment of the present invention.

FIGS. 5-7 illustrate various views of a therapeutic kit container in an open configuration, including various components being stored inside the container, according to an embodiment of the present invention.

FIG. 5 is a front perspective view from above of a therapeutic kit container in an open configuration including various components according to an embodiment of the present invention. FIG. 5. Illustrates a view that is similar to that of FIG. 4, except that a syringe 200, vial 300, and vial adapter 400 are in place in the container 101 in FIG. 5.

As illustrated in FIGS. 5 and 6 in particular, in an embodiment of the present invention, the first support wall 142 and the second support wall 144 of the first member 102 may work in concert with two hooks 150 of the first member 102 to hold a syringe 200 barrel 202 and the syringe 200 plunger rod 204 releasably in place via friction fitting.

Specifically, the syringe 200 barrel 202 and the syringe 200 plunger rod 204 may be placed into the first member 102 of the container 101 by putting the barrel 202 and the plunger rod 204 approximately in place and applying downward pressure to them such that the hooks 150 are temporarily bent, misaligned, or otherwise temporarily dislodged while the barrel 202 and the plunger rod 204 are moved into position. Eventually, the hooks 150 will have the freedom of movement to realign to their original position (or close to it) to accomplish the interference required to releasably hold the barrel 202 and the plunger rod 204 in place.

As illustrated in FIG. 5, in some embodiments, the first member 102 may be configured with open space to accommodate a backstop 206 (or finger flange) and a hub 208 of the barrel 202 of a syringe 200, and open space to accommodate a head 210 of the plunger rod 204 of a syringe 200. In other embodiments, the first member 102 may be specifically configured (e.g. with additional support walls, hooks, or other structural elements) with specific components for coupling to a backstop 206, hub 208, and/or head 210 of the syringe 200.

When it is desirable to remove the barrel 202 and the plunger rod 204 from the first member 102, upward pressure may be applied to the barrel 202 and the plunger rod 204 such that the hooks 150 are temporarily bent, misaligned, or otherwise temporarily dislodged while the barrel 202 and the plunger rod 204 are pulled out of the first member 102. Eventually, the hooks 150 will have the freedom of movement to realign to their original position (or close to it).

As illustrated in FIGS. 5-7, in an embodiment of the present invention, the sleeve 152 of the second member 104 may be configured to releasably hold a vial 300 or other vessel in the container 101. The second member 104 may include a cylindrical or frustoconically shaped sleeve 152 that may be suited to releasably hold a generally cylindrically shaped vial 300. In the embodiment depicted in FIG. 6, the sleeve 152 includes four upwardly extending walls equally spaced apart and defining four equally spaced apart voids. In some embodiments, the sleeve 152 may include fewer or greater than three upwardly extending walls and voids. The sleeve 152 may be centered on the inner surface 112 of the second member 104, or it may be offset from center.

Because of the configuration of this exemplary sleeve 152, in an embodiment, the sleeve may be configured to releasably hold the vial 200 by its base 304, as best illustrated by FIG. 7. In this manner, the vial 300 is held upright with its base 304 being securely grasped by the sleeve 152, and its cap 302 being presented upward away from the second member 104. The four walls of the sleeve 152 may work in concert to hold the vial 200 by its base 304 via friction fitting.

Specifically, the vial 300 may be placed into the second member 104 of the container 101 by putting the vial 300 approximately in place and applying downward pressure to it such that the four walls of the sleeve 152 are slightly deformed outward while the vial 300 is moved into position. In some embodiments, a generally cylindrically shaped sleeve 152 may apply pressure relatively equally along the height of the base 304 of the vial 300, while a generally frustoconically shaped sleeve 152 that tapers in an upward direction may apply slightly more pressure at a higher point of the base 304 of the vial 300.

As illustrated in FIGS. 5 and 6, in an embodiment of the present invention, the slots 154 and guides 156 of the third member 106 may be configured to releasably hold a vial adapter 400 in the container 101. As best illustrated in FIG. 6, slots 154 may consist of relatively short rails or tabs extending from the bottom and/or sides walls of the third member 106. As can be seen in FIG. 6, it may be possible to slide or bend and insert the skirt 404 of a vial adapter 400, or portions thereof, under one or more slots 154 to releasably secure the vial adapter 400 to the container 101.

As further depicted in FIG. 6, guides 156 may consist of relatively small bumps extending upward from the bottom surface of the third member 106. In an embodiment, it may be possible to slide or bend and insert the skirt 404 of a vial adapter 400, or portions thereof, past or over one or more guide 156 bumps to, in combination with one or more slots 154, releasably secure the vial adapter 400 to the container 101 via friction fitting.

Specifically, the vial adapter 400 may be slid or placed into the third member 106 of the container 101 by putting the vial adapter 400 approximately in place and applying a sliding pressure to it such that the skirt 404 of the vial adapter 400 flexes and passes over the guide 156 bumps, or by applying pressure to the flexible skirt 404 of the vial adapter 400 such that the edges of the flexible skirt 404 are temporarily bent or folded until they can fit underneath the slots 154.

Therapeutic kits 100 including containers 101, such as those described herein with respect to embodiments of the present invention, offer improved ergonomics, versatility, durability, and/or ease of use for patients and caregivers preparing and administering therapeutics. In some embodiments, the containers 101, possibly including first 102, second 104, and third 106 members, may be manipulated in a variety of ways between open and closed configurations to optimally conceal and present their contents to users.

In one embodiment, a container 101 may be configured such that in the closed configuration, as illustrated in FIG. 2, the outer surfaces 110 of the first 102 and third 106 members are approximately parallel to one another and facing opposite from one another, while in the open configuration, as illustrated in FIG. 4, the outer surfaces 110 of the first 102, second 104, and third 106 members are approximately parallel to one another and facing the same direction.

In another embodiment, a container 101 may be configured such that in the closed configuration, a top panel of the third member 106 and a bottom panel of the first member 102 are approximately parallel to one another, and a side panel, such as a side panel of the second member 104, is approximately perpendicular to the top and bottom panels. The container 101 may further be configured such that in the closed configuration, the side panel is configured to releasably hold a vial 300 in such a way that a longitudinal axis of the vial 300 (i.e. an axis running down the center of the vial 300 between its cap 302 and its base 304) would be approximately parallel to the top and bottom panels.

In yet another embodiment, a container 101 may be configured such that in the closed configuration, the longitudinal axis of the syringe 200 barrel 202 (i.e. an axis running down the center of the syringe 200 barrel 202 between its backstop 206 and its hub 208) is approximately parallel to the longitudinal axis of the vial 300, and in the open configuration, the longitudinal axis of the syringe 200 barrel 202 is approximately perpendicular to the longitudinal axis of the vial 300.

FIG. 7 is a right side view of a therapeutic kit container 101 in an open configuration including a disassembled syringe 200, vial 300, and vial adapter 400 according to an embodiment of the present invention. In contrast, FIG. 8 is a right side view of a therapeutic kit container 101 in an open configuration including the syringe 200, vial 300, and vial adapter 400 assembled together according to an embodiment of the present invention.

As previously discussed, the preparation and administration of a therapeutic liquid to an individual often involves the mixing of two or more medicaments or other substances to form the therapeutic liquid and the subsequent delivery of the mixed therapeutic liquid to the individual. The mixing of medicaments or other substances often involves extraction of one medicament or other substance in liquid form from a vial 300 or other vessel and transfer of this medicament or other substance into a separate vessel, such as a syringe 200, that holds the other medicament or substance.

Figure 8:
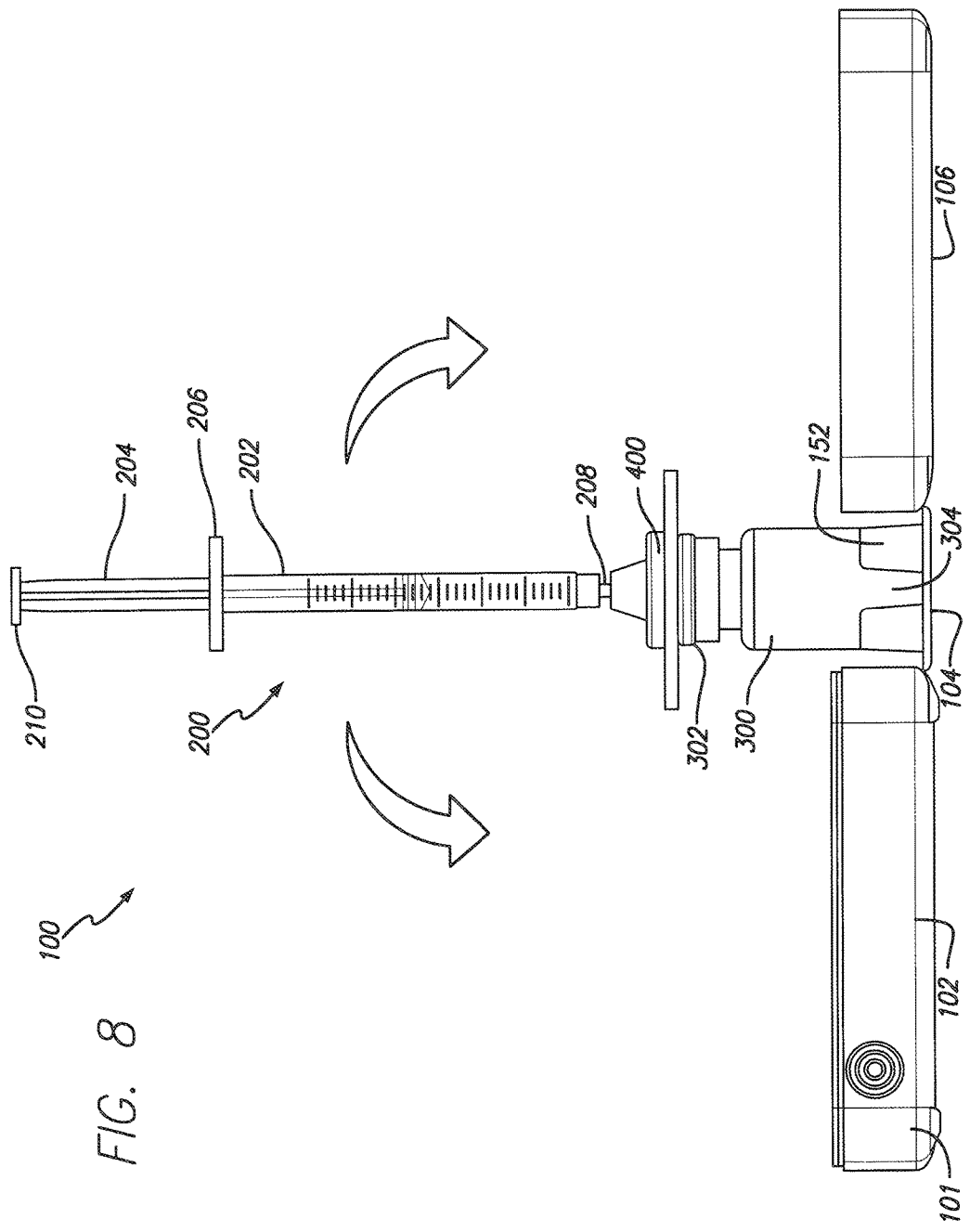
FIG. 8 is a right side view of a therapeutic kit container in an open configuration including various components assembled together according to an embodiment of the present invention.

Accordingly, with reference to FIG. 8, in an embodiment of the present invention, it may be desirable to connect the syringe 200, vial 300, and vial adapter 400 to prepare a therapeutic liquid. In one embodiment, the syringe 200 plunger rod 204 may be inserted into and locked to the syringe 200 barrel 202, the hub 208 of the syringe 200 barrel 202 may be attached to the connector 402 of the vial adapter 400, and an interior needle (not illustrated) of the vial adapter 400 may pierce through the cap 302 of the vial 300, while the skirt 404 of the vial adapter 400 rests upon the outer edges of the vial 300 cap 302.

An exemplary method for coupling the syringe 200, vial 300, and vial adapter 400 to prepare a therapeutic liquid for injection is now described. However, various other methods and sequences of steps may alternatively be used to accomplish therapeutic liquid preparation.

First, a user may open the container 101 such that the second member 104 lies flat on a preparation surface and the top of the cap 302 of the vial 300 is presented upward. Next, the user may remove the vial adapter 400 from the third member 106 of the container 101 by sliding the vial adapter 400 out of the slots 154 of other releasable holding mechanisms. Then the user may place the vial adapter 400 on top of the cap 302 of the vial 300 and push downward on the vial adapter 400 such that the an interior needle (not illustrated) of the vial adapter 400 may pierce through the cap 302 of the vial 300. In other embodiments, the vial adapter 400 and vial 300 may be connected by mechanisms other than by having an interior needle of the vial adapter 400 pierce through the cap 302 of the vial 300. For example, the vial adapter 400 may include a fastener mechanism capable of mating with a compatible fastener mechanism of the cap 302 of the vial 300. Suitable fastener mechanisms may include, for example, a plastic Luer lock or other suitable threaded, friction fit, or other fastening means.

Next, the user may remove the barrel 202 and the plunger rod 204 of the syringe 200 from the first member 102 of the container 101 by releasing them from the first support wall 142, second support wall 144, hooks 150, or other releasable holding mechanisms. The user may then assemble the barrel 202 and the plunger rod 204 of the syringe 200 together to form a complete syringe 200. At this point, the user may connect the syringe 200 to the vial adapter 400 by connecting the syringe 200 hub 208 to the connector 402 of the vial adapter. The connector 402 of the vial adapter and/or the hub 208 of the syringe may include fastener mechanisms capable of mating with a compatible fastener mechanism of each other. Suitable fastener mechanisms may include, for example, a plastic Luer lock. Luer cone, Luer slip, or other suitable threaded, friction fit, or other fastening means.

Assembling a syringe 200, vial adapter 400, and vial 300 into a long, continuous structure, as illustrated in FIG. 8 and described above, can be difficult for patients and caregivers. Some individuals prefer to try to assemble the structure in an upright fashion with the base of the vial 300 resting on a level surface, such as a tabletop, with the head 210 of the syringe 200 plunger rod 204 pointing upward. However, this arrangement can be very unstable and prone to toppling over in response to the slightest environmental disturbances, such as a slight vibration or movement of a table that the arrangement is stacked upon. The point at which the user presses downward on the vial adapter 400 such that the an interior needle of the vial adapter 400 pierces through the cap 302 of the vial 300 is a particularly vulnerable time when the entire apparatus may topple over if not stable. Similar potential instability may also occur when the user connects the syringe 200 to the vial adapter 400 by connecting the syringe 200 hub 208 to the connector 402 of the vial adapter. In addition, as a substance is drawn into the syringe 200 from the vial 300, the arrangement becomes top-heavy, thus further destabilizing it.

According to an embodiment of the present invention, these problems may be solved by configuring the container 101 such that patient or caregiver can assemble the syringe 200, vial adapter 400, and vial 300 together while these elements are supported by the container 101 itself. This may be accomplished by building the continuous structure of elements starting with the vial 300, which may be removably secured by the container 101.

Moreover, according to embodiments of the present invention, the container 101 may be configured such that the base 304 of the vial 300 may be removably secured to the container 101 while the cap 302 of the vial is displayed upwardly and freely engaged by the vial adapter 400, while the base 304 of the vial 300 is still held in position.

Additionally, according to embodiments of the present invention the container 101 may secure the vial 300 in such a way that when the container 101 is manipulated from its closed configuration to its open configuration, the vial 300 does not have to be moved or otherwise reoriented, but is automatically in the proper position to be engaged by the vial adapter 400. In this way, regardless of the way the vial 300 is oriented during storage, the cap 302 of the vial 300 may be upwardly displayed in the open configuration.

In embodiments employing a first member 102, second member 104, and third member 106, as described above, the arrangement of the container 101 may provide a further advantage in that first member 102 and the third member 106 may provide wide, stable bases with which to ground and support the central second member 102 including the sleeve 152 acting as the base for the vial 300. As illustrated in FIG. 8, in this configuration, were forces to act upon the syringe 200, vial adapter 400, vial 300 arrangement to potentially destabilize it (as illustrated by curved arrows), the stable base provided by the interconnected first member 102, second member 104, and third member 106 could resist such forces.

In some embodiments of the present invention, portions of the first member 102, second member 104, and/or third member 106 that may contact a working surface (such as a table) during assembly may be specifically adapted to increase the friction between the container 101 and the working surface to further stabilize the arrangement. For example, in some embodiments, increased texture maybe provided by using materials such as rubber, or by scoring, stippling, adding dimples, ridges, or other textural surface elements.

Accordingly, such a container 101 configuration may be capable of providing improved ergonomics, versatility, durability, and/or ease of use.

In addition, as perhaps best illustrated in FIG. 4, in some embodiments, when the vial adapter 400 is removed from the third member 106 to be placed on the cap 302 of the vial, the inner surface 112 of the third member 106 becomes an essentially open, sterile working area. This open space may advantageously be used as a working or staging area to temporarily set or store the syringe 200, retracted vial adapter 400, or other ancillary elements (e.g. instructions, an infusion needle set, alcohol swabs, gauze pads, or band-aids) while preparing for an injection.

In some embodiments of the present invention, when the user has finished using the elements of the therapeutic kit 100 container 101 for their intended purpose (e.g. to administer an injection), the elements may be placed back in the container 101 to be discarded. In embodiments where the container 101 is made from a durable material, such as a durable polypropylene, and has a suitable closure mechanism, such as closure element 140, the container 101 may serve as a durable, secure means to dispose of potentially dangerous and/or hazardous items such as needles of a syringe 200.

Figure 9A:
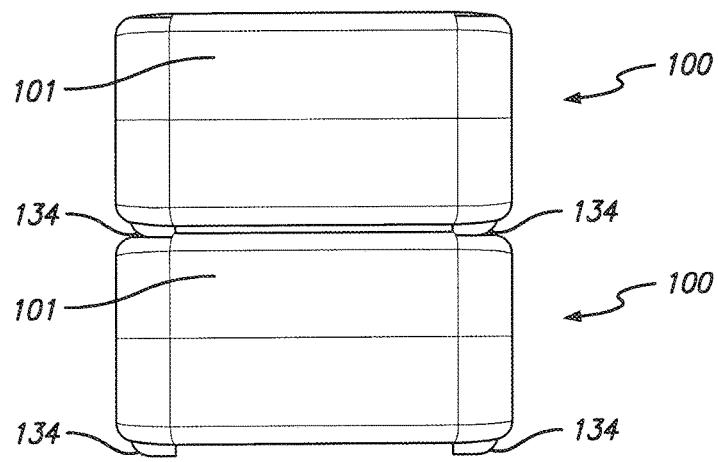
FIG. 9A is a front view of two therapeutic kit containers stacked on top of one another in closed configurations according to an embodiment of the present invention.
Figure 9B:
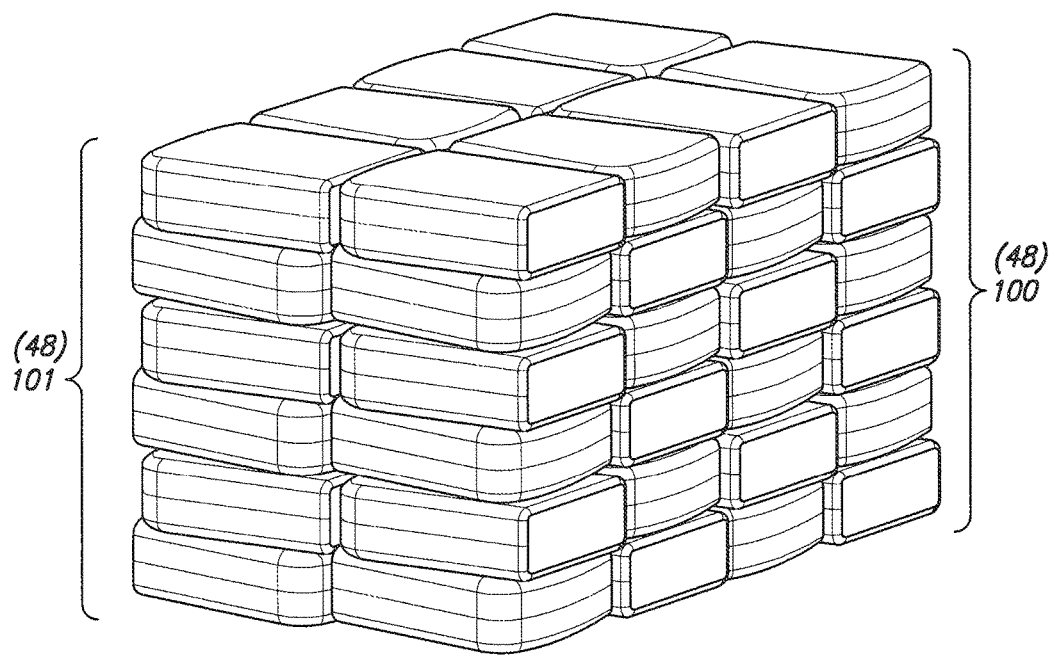
FIG. 9B is a front view of forty-eight therapeutic kit containers stacked on top of one another in closed configurations according to an embodiment of the present invention.

With reference to FIGS. 9A and 9B, in their closed configurations, containers 101 according to embodiments of the present invention may be capable of being stacked and stored in large quantities due to their ergonomic features and compact size.

In FIG. 9A, a first container 101 is stacked on top of a second container 101. As explained above, the upper container 101 may include a plurality of bottom mating elements 134 on the outer surface 110 of its first member 102, while the lower container 101 may include a plurality of top mating elements 132 on the outer surface 110 of its third member 106. The bottom mating elements 134 of one container 101 may mate with complementary top mating elements 132 of the other container 101 to allow multiple containers 101 to be conveniently and securely stacked for storage or travel.

FIG. 9B illustrates forty-eight individual containers 101 stacked upon one another. Certain diseases or medical conditions may require the administration of medicaments that only remain stable for significant periods of time while under refrigeration. To the extent that these same diseases or medical conditions may require frequent (e.g. daily) dosing, it may be important to patients and caregivers to be able to store large quantities of the medicaments under refrigeration so that multiple trips to the medicament vendor need not be made. Common restrained refrigeration environments may include, for example, household refrigerators, dormitory refrigerators, or hospital refrigerators.

To the extent that such medicaments are most conveniently distributed and used as a part of therapeutic kits 100, the containers 101 for such kits 100 should be as small and easily stackable as possible. Accordingly, containers 100 according to embodiments of the present invention described above having relatively compact dimensions in addition to convenient, ergonomic stacking features may provide advantages to patients or caregivers having bulk storage needs.

In some embodiments for use with medicaments, such as, for example, medicaments that require refrigeration to remain stable, it may be desirable to increase the level of thermal insulation of the container 101. In this way, the container (and medicament carried within in) will remain cooler longer even if a user carries the container 101 while traveling in a non-refrigerated traveling bag, such as a backpack, purse, diaper bag, or luggage, in a warm environment. In one embodiment, the container 101 is thermally insulated by thickening the walls of the container 101 that make up the first 102, second 104, and third 106 members. In another embodiment, the container 101 is thermally insulated by applying additional insulating layers to the container 101, such as layers made from, for example, mineral wool, glass wool, flexible elastomeric foams, rigid foams, polyethylene, silica aerogel insulation, or bladders filled with gasses or liquids such as air or water.

Figure 10:
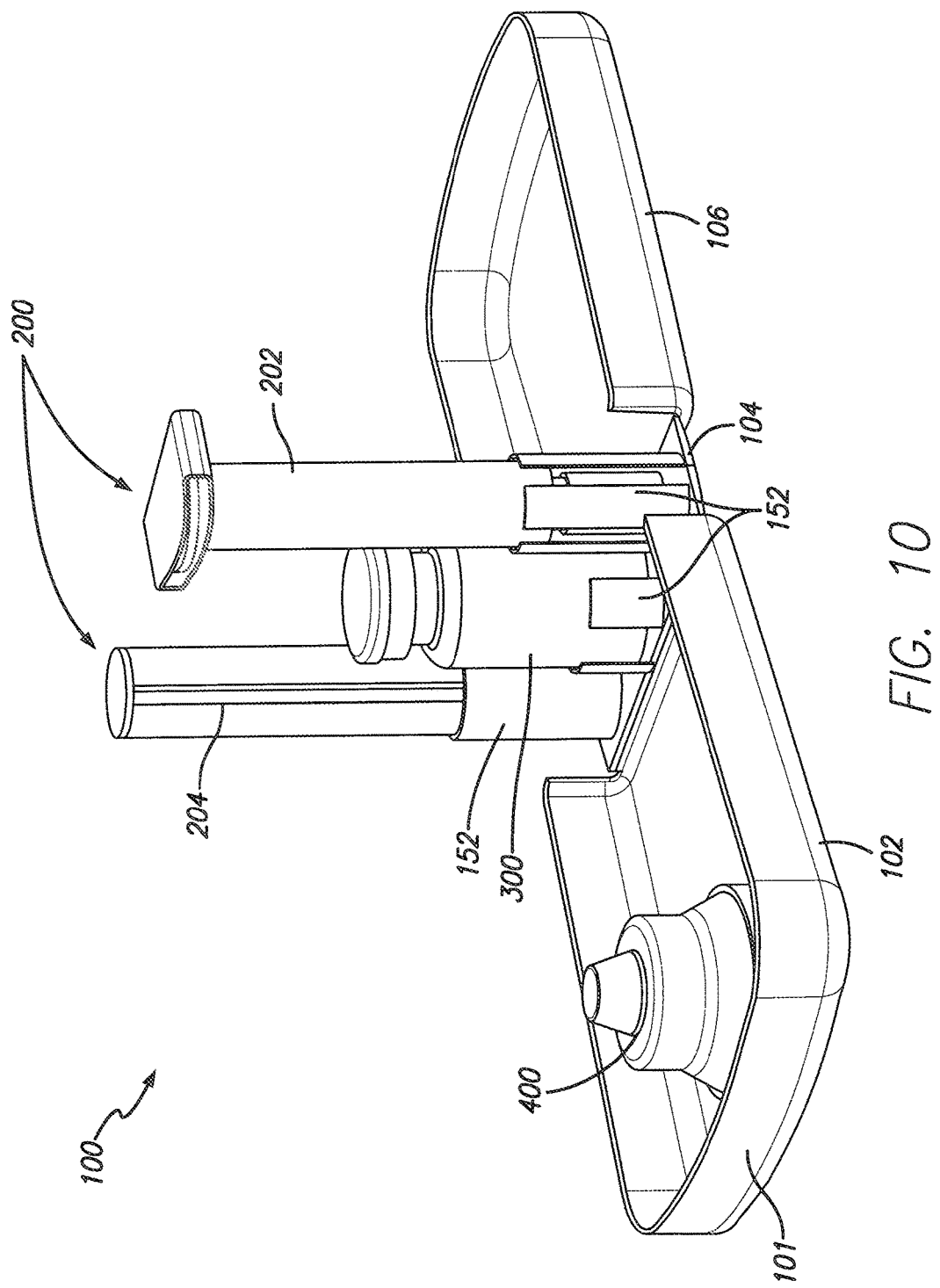
FIG. 10 is a front perspective view from above of a therapeutic kit container in an open configuration including various components according to an alternative embodiment of the present invention.

FIG. 10 is a front perspective view from above of a therapeutic kit 100 container 101 in an open configuration including various components according to an alternative embodiment of the present invention.

In contrast with the interior surfaces 112 of the therapeutic kit 100 containers 101 illustrated in FIGS. 1 and 4-6, it should be noted that this alternative container 101 is configured to store some of the syringe 200, vial 300, and vial adapter 400 in different locations that previously described above. Specifically, in the embodiment of FIG. 10, in addition to the vial 300, the syringe 200 barrel 202 and the syringe plunger rod 204 are also both releasably secured in the central second member 104 of the container 101. Accordingly, while one of the first member 102 and the third member 106 are left to house the vial adapter 400, the other of these members is left as an open, sterile working area. This working area may be advantageously used to temporarily set or store the syringe 200, retracted vial adapter 400, or other ancillary elements (e.g. product instructions, an infusion needle set, alcohol swabs, gauze pads, or band-aids) while preparing for an injection.

While the medical components potentially housed by containers 101 according to embodiments of the present invention discussed herein have primarily been a syringe 200, a vial 300, and a vial adapter, in other embodiments, the container 101 may be configured to store and/or releasably hold product instructions, an infusion needle set, alcohol swabs, gauze pads, or band-aids. In some embodiments, these ancillary elements may be alternatively be stored and/or held in a larger outer packaging container that may be used to store and secure the container 101 at various points in time during manufacture, distribution, sale, and/or use.

In other embodiments, a single container 101 may be configured to hold multiple syringes 200, multiple vials 300, and/or multiple vial adapters. In various embodiments, the second member 104 may be configured to hold one, two, three, four, five, or more vials 300.

In addition, while exemplary embodiments of the present invention have been described as releasably holding specific components at either the first 102, second 104, or third 106 member of a container, the present invention need not be so limited. In some embodiments, a syringe 200 may be releasably held by either the first 102, second 104, or third 106 member, the vial 300 may be held by either the first 102, second 104, or third 106 member, and the vial adapter 400 may be held by either the first 102, second 104, or third 106 member. In an embodiment, each of the syringe 200, vial 300, and vial adapter 400 may all he releasably held by a single one of the first 102, second 104, or third 106 member.

Furthermore, while many of the exemplary embodiments of the present invention have been described in the context of containers 101 with a first 102, second 104, and third 106 member, containers 101 according to other embodiments of the present invention may have fewer or greater than three members.

In some embodiment of the present invention, different kits 100 and/or containers 101 may be designed for different therapeutics or doses thereof. For example, certain containers 101 may hold certain therapeutics having different concentrations, volumes, and/or strengths. In an embodiment, a portion of each container 101 may be colored with a specific color, wherein the container 101 is color coded to indicate the type of therapeutic and/or the dose of the therapeutic that it contains.

In another embodiment of the present invention, parts of the kits 100 and/or containers 101 may include portions having product labeling. Labeling may be included by the addition of label stickers or by having the labeling printed, caved, molded, or otherwise formed on or in parts of the kits 100 and/or containers 101. In some embodiments the kits 100 and/or containers 101 are labeled to indicate the type and/or dose of the therapeutic that they contain. In some embodiments, labeling may be part of a larger outer packaging container for containing the container 101, a sleeve surrounding the container 101. or other suitable means.

As previously discussed, therapeutic kits 100 may be sold for a wide variety of medicaments. In one embodiment of the present invention, a therapeutic kit 100 container 101 is configured for use with a hemophilia treatment kit.

Hemophilia is one of the most common inherited coagulation disorders in the world. It results in decreased in vivo and in vitro blood clotting activity, and requires extensive medical monitoring throughout the life of the affected individual. In the absence of intervention, the individual affected by will suffer from spontaneous bleeding often leading to serious medical complications. In hemophilia, coagulation is disturbed by a lack of certain plasma blood clotting factors. For example, hemophilia A is caused by a deficiency in Factor VIII (FVIII), while hemophilia B is caused by a deficiency in Factor IX (FIX). Each of these forms of hemophilia may result from either the decreased synthesis of the relevant blood clotting factor protein (e.g. FVIII or FIX) or a defective blood clotting factor protein with reduced activity.

The treatment of hemophilia occurs by replacing the missing blood clotting factor protein by exogenous factor concentrates highly enriched in the missing clotting factor. The necessary blood clotting factor proteins are typically administered at least several times a week via intravenous injections to the individual affected by hemophilia using a syringe 200. While some affected individuals may receive injections from a caregiver, many individuals chose to self-administer injections, often for reasons of cost and convenience.

Because individuals affected by hemophilia are highly susceptible to accidental bleeding in everyday situations, stress points on tools (e.g. containers 101), stress points generated by environmental surfaces (e.g. the surface or edge of a table), and stresses resulting from unnatural movements of the body have the potential to cause microbleeds as the individual interacts with tools in their environment. In the case of routine injections a therapeutic kit 100, particularly for affected individuals who self-administer treatments, even small positive changes in container 101 configurations and the movements necessary to manipulate the container 101 and assemble its contents have the potential to minimize microbleeds or other injuries to the individual.

Accordingly, therapeutic kit 100 containers 101 offering improved ergonomics, versatility, durability, and/or ease of use according to embodiments of the present invention may provide advantages to patients or caregivers administering hemophilia treatments.

Because of the advantages of therapeutic kit 100 containers 101 according to embodiments of the present invention, these containers may be equally suited for the administration of other medicaments for patients or caregivers with similar requirements (i.e. ergonomic, versatile, durable, and easy to use), such as, for example, arthritis patients.

It will be noted that while the present discussion focuses primarily on therapeutic kit 100 containers 101, some embodiments of the device containers described herein need not be limited to use with therapeutic kits, and may be suitable for storing items for a variety of non-therapeutic and non-medical purposes.

The present invention has been described above by way of exemplary embodiments. Accordingly, the present invention should not be limited by any of the above-described exemplary embodiments, but should be defined only in accordance with the following claims and their equivalences.

What is claimed is:

1. A medical device kit container comprising:
   a first member configured to releasably hold a syringe barrel;
   a second member configured to releasably hold a vial, wherein the second member is coupled to the first member by a first hinge; and
   a third member coupled to the second member by a second hinge,
   wherein the container is configured to provide stability to the syringe barrel when a bottom surface of the second member lies flat on a preparation surface when the syringe barrel is coupled to the vial while the vial is releasably held in an upright position, and
wherein the container is further configured such that a user can couple the syringe barrel to the vial without first releasing the vial from the second member.

2. The container of claim 1, wherein the first, second, and third members are formed as a unitary structure.

3. A medical device kit comprising:
a syringe barrel;
a vial having a cap and a base; and
a container for holding the syringe barrel and the vial, the container comprising:
a first member;
a second member configured to releasably hold the vial by its base, the second
member coupled to the first member by a first hinge; and
a third member coupled to the second member by a second hinge,
wherein the container is configured such that a user may couple the syringe barrel to the cap of the vial without first releasing the vial from the second member, and
wherein the container is further configured such that it can provide stability to the syringe barrel when a bottom surface of the second member lies flat on a preparation surface when the syringe barrel is coupled to the vial while the vial is releasably held in position.

4. A medical device kit comprising:
a syringe barrel having a longitudinal axis;
a vial having a longitudinal axis; and
a container for holding the syringe barrel and the vial, wherein the container has a closed configuration and an open configuration, the container comprising:
a first member configured to releasably hold the syringe barrel;
a second member configured to releasably hold the vial,
wherein the longitudinal axis of the syringe barrel is approximately parallel to the longitudinal axis of the vial when the container is in its closed position,
wherein the longitudinal axis of the syringe barrel is approximately perpendicular to the longitudinal axis of the vial when the container is in its open position, and
wherein the container is configured such that it can provide stability to the syringe barrel when a bottom surface of the second member lies flat on a preparation surface when the syringe barrel is coupled to the vial while the vial is releasably held in position.

5. The medical device kit of claim 4, wherein the container is configured such that a user can couple the syringe barrel to the vial without first releasing the vial from the second member.

6. A medical device kit comprising:
a vial;
a syringe barrel; and
a container for holding the syringe barrel and the vial, the container comprising:
a first member;
a second member configured to releasably hold the vial in an upright position, the second member coupled to the first member by a hinge; and
a third member,
wherein the container is configured to provide stability to the vial when a bottom surface of the second member lies flat on a preparation surface such that the vial is releasably held in the upright position, and
wherein the container is further configured to provide stability to the syringe barrel when the syringe barrel is coupled to the vial when the bottom surface of the second member lies flat on the preparation surface such that the vial is releasably held in the upright position.

7. The medical device kit of claim 6, wherein the container is configured such that a user can couple the syringe barrel to the vial without first releasing the vial from the second member.

8. The container of claim 1, wherein the first member is configured to releasably hold the syringe barrel via a friction fitting.

9. The container of claim 1, wherein a sleeve of the second member is configured to releasably hold the vial by its base.

10. The container of claim 1, wherein the third member is configured to releasably hold a vial adapter.

11. The container of claim 1,
wherein the container has a closed configuration and an open configuration,
wherein the container is configured such that in the closed configuration, the outer surfaces of the first and third members are approximately parallel to one another and facing opposite from one another, and
wherein the container is configured such that in the open configuration, the outer surfaces of the first, second, and third members are approximately parallel to one another and facing the same direction when lying flat on a preparation surface.

12. The medical device kit of claim 3, wherein a sleeve of the second member is configured to releasably hold the vial by its base.

13. The medical device kit of claim 3,
wherein the container has a closed configuration and an open configuration,
wherein the longitudinal axis of the syringe barrel is approximately parallel to the longitudinal axis of the vial when the container is in its closed position, and
wherein the longitudinal axis of the syringe barrel is approximately perpendicular to the longitudinal axis of the vial when the container is in its open position and lying flat on a preparation surface.

14. The medical device kit of claim 3, further comprising:
a vial adapter,
wherein the vial adapter is configured to couple a hub of the syringe barrel to the cap of the vial.

15. The medical device kit of claim 4, further comprising:
a syringe plunger rod having a longitudinal axis,
wherein the first member of the container is further configured to releasably hold the syringe plunger rod.

16. The medical device kit of claim 15, wherein the first member of the container is further configured to hold the syringe barrel and the syringe plunger rod separate from one another in a disassembled state.

17. The medical device kit of claim 16, wherein the first member of the container is further configured to hold the syringe barrel and the syringe plunger rod such that the longitudinal axis of the syringe barrel is approximately parallel to the longitudinal axis of the syringe plunger regardless of whether the container is in its closed position or the open position.

18. The medical device kit of claim 4, wherein the first member is configured to releasably hold the syringe barrel via a friction fitting.

19. The medical device kit of claim 4, wherein a sleeve of the second member is configured to releasably hold the vial by its base.

20. The medical device kit of claim 6, wherein a sleeve of the second member is configured to releasably hold the vial by its base.

21. The medical device kit of claim 6, further comprising:
a vial adapter,
wherein the vial adapter is configured to couple a hub of the syringe barrel to a cap of the vial.

* * * * *